US008357783B2

(12) United States Patent
Dimitrov et al.

(10) Patent No.: US 8,357,783 B2

(45) Date of Patent: Jan. 22, 2013

(54) HUMAN ANTI-MESOTHELIN MONOCLONAL ANTIBODIES

(75) Inventors: Dimiter S. Dimitrov, Frederick, MD (US); Yang Feng, Frederick, MD (US); Ira H. Pastan, Potomac, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 302 days.

(21) Appl. No.: 12/934,060

(22) PCT Filed: Mar. 25, 2009

(86) PCT No.: PCT/US2009/038228

§ 371 (c)(1), (2), (4) Date: Sep. 22, 2010

(87) PCT Pub. No.: WO2009/120769

PCT Pub. Date: Oct. 1, 2009

(65) Prior Publication Data

US 2011/0020361 A1 Jan. 27, 2011

Related U.S. Application Data

(60) Provisional application No. 61/040,005, filed on Mar. 27, 2008.

(51) Int. Cl.

| | |
|---|---|
| ***C07K 16/00*** | (2006.01) |
| ***A61K 39/395*** | (2006.01) |
| ***G01N 33/53*** | (2006.01) |

(52) U.S. Cl. ............ 530/388.25; 530/388.1; 530/387.1; 424/156.1; 424/141.1; 424/133.1; 424/130.1; 435/7.1

(58) Field of Classification Search ........................ None
See application file for complete search history.

(56) References Cited

U.S. PATENT DOCUMENTS

| | | | | |
|---|---|---|---|---|
| 5,789,650 | A | 8/1998 | Lonberg et al. | |
| 5,798,230 | A | 8/1998 | Bornkamm et al. | |
| 6,083,502 | A | 7/2000 | Pastan et al. | |
| 6,146,894 | A | 11/2000 | Nicolaides et al. | |
| 6,153,430 | A | 11/2000 | Pastan et al. | |
| 6,770,445 | B1 | 8/2004 | Scholler et al. | |
| 6,809,184 | B1 | 10/2004 | Pasta et al. | |
| 7,081,518 | B1 | 7/2006 | Pastan et al. | |
| 7,368,110 | B2 * | 5/2008 | Pastan et al. | 424/133.1 |
| 2005/0054056 | A1 | 3/2005 | Ebel et al. | |
| 2005/0123900 | A1 | 6/2005 | Dimitrov et al. | |
| 2005/0214304 | A1 | 9/2005 | Pastan et al. | |
| 2006/0204506 | A1 | 9/2006 | Ebel et al. | |
| 2007/0292390 | A1 | 12/2007 | Dimitrov et al. | |

FOREIGN PATENT DOCUMENTS

| | | | |
|---|---|---|---|
| EP | 0 871 492 | B1 | 11/2003 |
| WO | WO 00/73346 | A1 | 12/2000 |
| WO | WO 2005/014652 | A1 | 2/2005 |
| WO | WO 2006/099141 | A2 | 9/2006 |
| WO | WO 2006/113643 | A2 | 10/2006 |
| WO | WO 2006/124641 | A2 | 11/2006 |
| WO | WO 2007/118214 | A2 | 10/2007 |

OTHER PUBLICATIONS

Bera et al., "Bivalent Disulfide-stabilized Fragment Variable Immunotoxin Directed against Mesotheliomas and Ovarian Cancer," *Molecular Cancer Therapeutics, American Association of Cancer Research* 1(2):79-84, Dec. 1, 2001.

Bergan et al., "Development and in vitro validation of anti-mesothelin biobodies that prevent CA125/Mesothelin-dependent cell attachment," *Cancer Letters* 255:263-274, 2007.

Chang et al., "Control of human mesothelin-expressing tumors by DNA vaccines," *Gene Therapy* 14:1189-1198, 2007.

Chang et al., "Molecular cloning of mesothelin, a differentiation antigen present on mesothelium, mesotheliomas, and ovarian cancers," *Proc. Natl. Acad. Sci. U.S.A.* 93:136140, Jan. 1996.

Chowdhury et al., "Improving antibody affinity by mimicking somatic hypermutation in vitro," *Nature Biotechnology* 17(1):568-572, Jun. 1, 1999.

Chowdhury et al., "Isolation of a high-affinity stable single-chain Fv specific for mesothelin from DNA-immunized mice by phage display and construction of a recombinant immunotoxin with anti-tumor activity," *Proc. Natl. Acad. Sci. U.S.A.* 95(2):669-674, Jan. 1, 1998.

Fan et al., "Targeted Therapy against Human Lung Cancer in Nude Mice by High-Affinity Recombinant Antimesothelin Single-Chain Fv Immunotoxin[1]," *Molecular Cancer Therapeutics* 1:595-600, Jun. 2002.

Hassan et al., "Mesothelin targeted cancer immunotherapy," *European Journal of Cancer* 44(1):46-53, Oct. 22, 2007.

Hassan et al., "Preclinical evaluation of MORAb-009, a chimeric antibody targeting tumor-associated mesothelin," *Cancer Immunity* 7:20, Dec. 19, 2007.

Hassan et al., "Mesothelin: A new Target for Immunotherapy," *Clinical Cancer Research* 10:3937-3942, Jun. 15, 2004.

Hassan et al., "Antitumor Activity of SS(dsFv)PE38 and SS1(dsFv)PE38, Recombinant Antimesothelin Immunotoxins against Human Gynecologic Cancers Grown in Organotypic Culture in Vitro," *Clinical Cancer Research* 8:3520-3526, Nov. 2002.

Ho et al., "Mesothelin Expression in Human Lung Cancer," *Clin. Cancer Res.* 13(5):1571-1575, Mar. 1, 2007.

(Continued)

*Primary Examiner* — Sharon Wen

(74) *Attorney, Agent, or Firm* — Klarquist Sparkman, LLP

(57) ABSTRACT

Disclosed herein are isolated human monoclonal antibodies that specifically bind human mesothelin with a binding affinity of about 25 nM or less. Nucleic acids encoding these antibodies, expression vectors including these nucleic acid molecules, and isolated host cells that express the nucleic acid molecules are also disclosed. The antibodies can be used to detect human mesothelin in a sample. Methods of diagnosing cancer, or confirming a diagnosis of cancer, are disclosed herein that utilize these antibodies. Methods of treating a subject with cancer are also disclosed.

23 Claims, 4 Drawing Sheets

OTHER PUBLICATIONS

Li et al., "Human antibodies for immunotherapy development generated via a human B cell hybridoma technology," *Proc. Natl. Acad. Sci. U.S.A.* 103(10):3557-3562, Mar. 7, 2006.

Onda et al., "New Monoclonal Antibodies to Mesothelin Useful for Immunohistochemistry, Fluorescence-Activated Cell Sorting, Western Blotting, and ELISA," *Clinical Cancer Research* 11(16):5840-5846, Aug. 15, 2005.

Presta et al., "Engineering of therapeutic antibodies to minimize immunogenicity and optimize function," *Advanced Drug Delivery Reviews* 58(5-6):640-656, Aug. 7, 2006.

Sato et al., "Pretargeted Radioimmunotherapy of Mesothelin-Expressing Cancer Using a Tetravalent Single-Chain Fv-Streptavidin Fusion Protein," *The Journal of Nuclear Medicine* 46(7):1201-1209, Jul. 2005.

Weiner, "Fully Human Therapeutic Monoclonal Antibodies," *Journal of Immunotherapy* 29(1):1-9, Jan./Feb. 2006.

Zhang et al., "Synergistic Antitumor Activity of Taxol and Immunotoxin SS1P in Tumor-Bearing Mice," *Clin. Cancer Res.* 12(15):79-84, Aug. 1, 2006.

Zhang et al., "Selection of a Novel gp41-specific HIV-1 Neutralizing Human Antibody by Competitive Antigen Panning," *J. Immunol Methods* 317(1-2):21-30, Dec. 20, 2006.

Zhu et al., "Potent Neutralization of Hendra and Nipah Viruses by Human Monoclonal Antibodies," *Journal of Virology* 80(2):891-899, Jan. 2006.

International Search Report and Written Opinion for PCT/US2009/038228, dated Jun. 30, 2010, 15 pages.

* cited by examiner

HUMAN ANTI-MESOTHELIN MONOCLONAL ANTIBODIES

CROSS REFERENCE TO RELATED APPLICATIONS

This is the U.S. National Stage of International Application No. PCT/US2009/038228, filed Mar. 25, 2009, published in English under PCT Article 21(2), which claims the benefit of U.S. Provisional Application No. 61/040,005, filed Mar. 27, 2008. The provisional application is herein incorporated by reference in its entirety.

FIELD

This disclosure relates to fully human monoclonal antibodies, particularly human monoclonal antibodies that specifically bind mesothelin, and their use.

BACKGROUND

Human mesothelin is a 40 kDa cell-surface glycosylphosphatidylinositol (GPI)-linked glycoprotein. The protein is synthesized as a 69 kD precursor which is then proteolytically processed. The 30 kD amino terminus of mesothelin is secreted and is referred to as megakaryocyte potentiating factor (Yamaguchi et al., *J. Biol. Chem.* 269:805 808, 1994). The 40 kD carboxyl terminus remains bound to the membrane as mature mesothelin (Chang et al., *Natl. Acad. Sci. USA* 93:136 140, 1996).

Mesothelin is present at relatively low levels in mesothelial cells of the pleura, peritoneum and pericardium of healthy individuals, but is highly expressed in a number of different cancers, including mesotheliomas, stomach cancer, squamous cell carcinomas, prostate cancer, pancreatic cancer, lung cancer, and ovarian cancer (Hassan et al., *Clin. Cancer Res.* 10:3937-3942, 2004; McGuire et al., *N. Engl. J. Med.* 334:1-6, 1996; Argani et al., *Clin. Cancer Res.* 7:3862-3868, 2001; Hassan et al., *Appl. Immunohistochem. Mol. Morphol.* 13:243-247, 2005; Li et al., *Mol. Cancer. Ther.* 7:286-296, 2008; U.S. Pat. No. 7,081,518). In particular, it has been reported that a majority of serous carcinomas of the ovary and adenocarcinomas of the pancreas express high levels of mesothelin (Yen et al., *Clin. Cancer Res.* 12:827-831, 2006). In addition, high levels of mesothelin have been detected in greater than 55% of lung cancers and greater than 70% ovarian cancers (Hassan et al., *Appl. Immunohistochem. Mol. Morphol.* 13:243-247, 2005; Ho et al., *Clin. Cancer Res.* 13(5):1571-1575, 2007). The limited expression of mesothelin on normal cells makes it a viable target for tumor immunotherapy.

Mesothelin can also be used a marker for diagnosis and prognosis of certain types of cancer because trace amounts of mesothelin can be detected in the blood of some patients with mesothelin-positive cancers (Cristaudo et al., *Clin. Cancer Res.* 13:5076-5081, 2007). It has been reported that mesothelin may be released into serum through deletion at its carboxyl terminus or by proteolytic cleavage from its membrane bound form (Hassan et al., *Clin. Cancer Res.* 10:3937-3942, 2004). An increase in the soluble form of mesothelin was detectable several years before malignant mesotheliomas occurred among workers exposed to asbestos (Creaney and Robinson, *Hematol. Oncol. Clin. North Am.* 19:1025-1040, 2005). Furthermore, patients with ovarian, pancreatic, and lung cancers also have elevated soluble mesothelin in serum (Cristaudo et al., *Clin. Cancer Res.* 13:5076-5081, 2007; Hassan et al.,

*Clin. Cancer Res.* 12:447-453, 2006; Croso et al., *Cancer Detect. Prev.* 30:180-187, 2006).

Mesothelin-specific antibodies have potential as cancer therapeutic and diagnostic reagents. A major limitation in the clinical use of mouse monoclonal antibodies is the development of a human anti-murine antibody (HAMA) response. The HAMA response can involve allergic reactions and an increased rate of clearance of the administered antibody from the serum. A need remains for fully human antibodies that specifically bind mesothelin with high affinity, which can be used in the diagnosis and treatment of cancer. However, it is difficult to produce fully human antibodies to human antigens, as these antigens are generally recognized as self antigens.

SUMMARY

Provided herein are isolated human monoclonal antibodies specific for human mesothelin. The antibodies were produced to human mesothelin using a human library. The human monoclonal antibodies bind mesothelin with a dissociation constant ($K_d$) of about 25 nM or less. In one embodiment, the $K_d$ is about 20 nM or less. In another embodiment, the $K_d$ is about 5 to about 10 nM. In some embodiments, the human monoclonal antibodies are Fab fragments. Further provided are compositions including the mesothelin-specific antibodies, nucleic acids encoding these antibodies, expression vectors comprising the nucleic acids, and isolated host cells that express the nucleic acids.

Also provided are immunoconjugates comprising the human monoclonal antibodies specific for human mesothelin. Compositions comprising the immunoconjugates are also provided.

The antibodies and compositions provided herein can be used for a variety of purposes, such as for diagnosing or for confirming the diagnosis of cancer in a subject. Thus, provided herein is a method of confirming the diagnosis of cancer in a subject, comprising contacting a sample from the subject diagnosed with cancer with a human monoclonal antibody that specifically binds mesothelin, and detecting binding of the antibody to the sample. An increase in binding of the antibody to the sample relative to binding of the antibody to a control sample confirms the cancer diagnosis. In some embodiments, the method further comprises contacting a second antibody that specifically recognizes the mesothelin-specific antibody with the sample, and detecting binding of the second antibody.

Similarly, provided herein is a method of detecting cancer in a subject, comprising contacting a sample from the subject with a human monoclonal antibody described herein, and detecting binding of the antibody to the sample. An increase in binding of the antibody to the sample relative to a control sample detects cancer in the subject. In some embodiments, the methods further comprise contacting a second antibody that specifically recognizes the mesothelin-specific antibody with the sample, and detecting binding of the second antibody.

Further provided is a method of treating a subject diagnosed with cancer, comprising administering a therapeutically effective amount of a human mesothelin-specific monoclonal antibody, or an immunoconjugate comprising the antibody, to the subject.

The foregoing and other features and advantages will become more apparent from the following detailed description of several embodiments, which proceeds with reference to the accompanying figures.

SEQUENCE LISTING

Figure 1A:
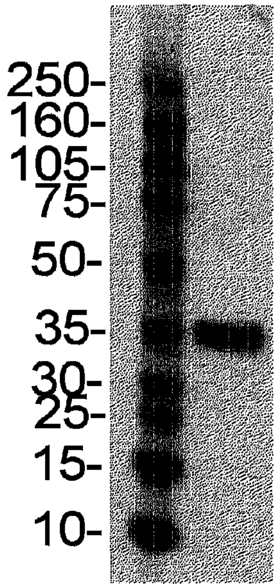
FIG. 1A is a digital image of an electrophoretic gel showing purified recombinant human mesothelin. A sample of recombinant human mesothelin purified from insect cell supernatant was run on a 4-12% NuPAGE™ Bis-Tris gel. Molecular weight standards are in kilodaltons (kD).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Sep. 17, 2010, 21.3 KB, which is incorporated by reference herein. In the accompanying sequence listing:

SEQ ID NO: 1 is the amino acid sequence of the light chain of mesothelin-specific antibody m912.

SEQ ID NO: 2 is the amino acid sequence of the heavy chain of mesothelin-specific antibody m912.

SEQ ID NOs: 3 and 4 are the nucleotide and amino acid sequences of human mesothelin, respectively, deposited under Genbank Accession No. AY743922 on May 17, 2005.

SEQ ID NO: 5 is the amino acid sequence of the ADPG tag for expression of recombinant mesothelin.

SEQ ID NO: 6 is the nucleotide sequence of the light chain of mesothelin-specific antibody m912.

SEQ ID NO: 7 is the nucleotide sequence of the heavy chain of mesothelin-specific antibody m912.

SEQ ID NO: 8 is the amino acid sequence of a peptide linker.

DETAILED DESCRIPTION

| I. Abbreviations | |
|---|---|
| 3SR | Self-sustained sequence replication |
| ADCC | Antibody-dependent cell-mediated cytotoxicity |
| CDR | Complementarity determining region |
| DNA | Deoxyribonucleic acid |
| DT | Diphtheria toxin |
| $EC_{50}$ | Effective concentration 50 |
| ELISA | Enzyme-linked immunosorbent assay |
| EM | Effector molecule |
| FACS | Fluorescence-activated cell sorting |
| FBS | Fetal bovine serum |
| FITC | Fluorescein isothiocyanate |
| GPI | Glycosylphosphatidylinositol |
| HAMA | Human anti-murine antibody |
| HRP | Horseradish peroxidase |
| Ig | Immunoglobulin |
| LCR | Ligase chain reaction |
| LDH | Lactate dehydrogenase |
| mAb | Monoclonal antibody |
| MHC | Major histocompatibility complex |
| MPBS | Milk/PBS |
| ORF | Open reading frame |
| PAGE | Polyacrylamide gel electrophoresis |
| PBMC | Peripheral blood mononuclear cells |
| PBS | Phosphate-buffered saline |
| PBST | PBS-Tween 20 |
| PCR | Polymerase chain reaction |
| PE | *Pseudomonas* exotoxin |
| RIA | Radioimmunoassay |
| SDS | Sodium dodecyl sulfate |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand comprising at least a light chain or heavy chain immunoglobulin variable region which specifically recognizes and binds an epitope of an antigen, such as mesothelin or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, $F(ab)'_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies) and heteroconjugate antibodies (such as, bispecific antibodies). See also, *Pierce Catalog and Handbook,* 1994-1995 (Pierce Chemical Co., Rockford, Ill.); Kuby, J., *Immunology,* $3^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined (see, Kabat et al., *Sequences of Proteins of Immunological Interest*, U.S. Department of Health and Human Services, 1991). The Kabat database is now maintained online The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds mesothelin will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds mesothelin.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

Binding affinity: Affinity of an antibody for an antigen. In one embodiment, affinity is calculated by a modification of the Scatchard method described by Frankel et al. (*Mol. Immunol.,* 16:101-106, 1979). In another embodiment, binding affinity is measured by an antigen/antibody dissociation rate. In another embodiment, a high binding affinity is measured by a competition radioimmunoassay. In another embodiment, binding affinity is measured by ELISA. In one embodiment, the antibodies disclosed herein bind human mesothelin with a dissociation constant ($K_d$) of about 25 nM or less. In several embodiments, the human monoclonal antibodies bind human mesothelin with a binding affinity of about 20 nM or less, about 15 nM or less, about 10 nM or less, about 5 nM or less, about 2.5 nM or less or about 1 nM or less. As used herein, a binding affinity of "about 20 nM" includes binding affinities of 19 to 21 nM. Similarly, a binding affinity of "about 25 nM" includes binding affinities of 24 to 26 nM.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In some embodiments, a chemotherapeutic agent is an agent of use in treating a mesothelioma, a prostate cancer, a lung cancer, a stomach cancer, a squamous cell carcinoma, a pancreatic tumor, an ovarian tumor, or another tumor. In some embodiments, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology 2$^{nd}$ ed., © 2000 Churchill Livingstone, Inc; Baltzer, L., Berkery, R. (eds.): *Oncology Pocket Guide to Chemotherapy,* 2nd ed. St. Louis, Mosby-Year Book, 1995; Fischer, D. S., Knobf, M. F., Durivage, H. J. (eds): *The Cancer Chemotherapy Handbook,* 4th ed. St. Louis, Mosby-Year Book, 1993). Combination chemotherapy is the administration of more than one agent to treat cancer. One example is the administration of an antibody that binds mesothelin or a fragment thereof used in combination with a radioactive or chemical compound.

Conservative variants: "Conservative" amino acid substitutions are those substitutions that do not substantially affect or decrease the affinity of an antibody to mesothelin. For example, a human antibody that specifically binds mesothelin can include at most about 1, at most about 2, at most about 5, and most about 10, or at most about 15 conservative substitutions and specifically bind the original mesothelin polypeptide. The term conservative variation also includes the use of a substituted amino acid in place of an unsubstituted parent amino acid, provided that antibody specifically binds mesothelin. Non-conservative substitutions are those that reduce an activity or binding to mesothelin.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Complementarity determining region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively.

Contacting: Placement in direct physical association; includes both in solid and liquid form.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant (of mesothelin): A polynucleotide encoding a mesothelin polypeptide or an antibody that binds mesothelin that includes a sequence that is degenerate as a result of the genetic code. There are 20 natural amino acids, most of which are specified by more than one codon. Therefore, all degenerate nucleotide sequences are included as long as the amino acid sequence of the mesothelin polypeptide or antibody that binds mesothelin encoded by the nucleotide sequence is unchanged.

Effector molecule (EM): The portion of a chimeric molecule that is intended to have a desired effect on a cell to which the chimeric molecule is targeted. Effector molecule is also known as an effector moiety, therapeutic agent, or diagnostic agent, or similar terms. In some embodiments disclosed herein, the EM is a toxin or a detectable label.

Therapeutic agents include such compounds as nucleic acids, proteins, peptides, amino acids or derivatives, glycoproteins, radioisotopes, lipids, carbohydrates, recombinant viruses or toxins. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-mesothelin antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm. Ther.* 28:341-365, 1985). Diagnostic agents or moieties include radioisotopes and other detectable labels. Detectable labels useful for such purposes are also well known in the art, and include radioactive isotopes such as $^{32}P$, $^{125}I$, and $^{131}I$, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide, such as mesothelin.

Expressed: Translation of a nucleic acid into a protein. Proteins may be expressed and remain intracellular, become a component of the cell surface membrane, or be secreted into the extracellular matrix or medium.

Framework region: Amino acid sequences interposed between CDRs. Framework regions include variable light and variable heavy framework regions. The framework regions serve to hold the CDRs in an appropriate orientation for antigen binding.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Human anti-murine antibody (HAMA) response: An immune response in a human subject to the variable and constant regions of a murine antibody that has been administered to the patient. Repeated antibody administration may lead to an increased rate of clearance of the antibody from the patient's serum and may also elicit allergic reactions in the patient.

Immune response: A response of a cell of the immune system, such as a B cell, T cell, or monocyte, to a stimulus. In one embodiment, the response is specific for a particular antigen (an "antigen-specific response"), such as mesothelin. In one embodiment, an immune response is a T cell response, such as a CD4+ response or a CD8+ response. In another embodiment, the response is a B cell response, and results in the production of specific antibodies.

Immunoconjugate: A covalent linkage of an effector molecule to an antibody. The effector molecule can be a detectable label or a toxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule. In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule.

Immunogenic peptide: A peptide, such as a mesothelin peptide, which comprises an allele-specific motif or other sequence, such as an N-terminal repeat, such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide. In one specific non-limiting example, an immunogenic polypeptide includes a region of mesothelin, or a fragment thereof, wherein the polypeptide that is expressed on the cell surface of a host cell that expresses the full-length mesothelin polypeptide.

Immunogenic composition: As used herein, an immunogenic composition is a composition comprising a mesothelin polypeptide that induces a measurable CTL response against cells expressing mesothelin polypeptide, or induces a measurable B cell response (such as production of antibodies) against a mesothelin polypeptide. It further refers to isolated nucleic acids encoding a mesothelin polypeptide that can be used to express the mesothelin polypeptide (and thus be used to elicit an immune response against this polypeptide). For in vitro use, an immunogenic composition may consist of the isolated protein or peptide epitope. For in vivo use, the immunogenic composition will typically comprise the protein or immunogenic peptide in pharmaceutically acceptable carriers, and/or other agents. Any particular peptide, such as a mesothelin polypeptide, or nucleic acid encoding the polypeptide, can be readily tested for its ability to induce a CTL or B cell response by art-recognized assays Immunogenic compositions can include adjuvants, which are well known to one of skill in the art.

Immunologically reactive conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane (*Antibodies, A Laboratory Manual*, Cold Spring Harbor Publications, New York, 1988) for a description of immunoassay formats and conditions. The immunologically reactive conditions employed in the methods are "physiological conditions" which include reference to conditions (such as temperature, osmolarity, and pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Mammal: This term includes both human and non-human mammals. Similarly, the term "subject" includes both human and veterinary subjects.

Major histocompatibility complex (MHC): Generic designation meant to encompass the histocompatibility antigen systems (class I and class II) described in different species, including the human leukocyte antigens ("HLA"). The term "motif" refers to the pattern of residues in a peptide of defined length, usually about 8 to about 11 amino acids, which is recognized by a particular MHC allele. The peptide motifs are typically different for each MHC allele and differ in the pattern of the highly conserved residues and negative binding residues.

Mesothelin: A mesothelin protein or fragment thereof that may be present on the surface of mammalian cells of a mammal, particularly humans. Exemplary nucleic acid and amino acid sequences of mesothelin are as described in PCT Publication No. WO 97/25,068; U.S. Pat. No. 6,083,502; Chang and Pastan, *Int. J. Cancer* 57:90, 1994; Chang and Pastan, *Proc. Natl. Acad. Sci. USA* 93:136, 1996; Brinkmann et al., *Int. J. Cancer* 71:638, 1997; and Chowdhury et al., *Mol. Immunol.* 34:9, 1997. Mesothelin also refers to mesothelin proteins or peptides which remain intracellular as well as secreted and/or isolated extracellular mesothelin protein.

Mesothelioma: A type of neoplasm derived from the lining cells of the pleura and peritoneum which grows as a thick sheet covering the viscera, and is composed of spindle cells or fibrous tissue which may enclose gland-like spaces lined by cuboidal cells. Mesotheliomas often originate in the tissue lining the lung, heart or abdomen. In some cases, mesotheliomas are caused by exposure to asbestos.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In several examples, a tumor is a mesothelioma, a prostate cancer or an ovarian cancer.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

Oligonucleotide: A linear polynucleotide sequence of up to about 100 nucleotide bases in length.

Open reading frame (ORF): A series of nucleotide triplets (codons) coding for amino acids without any termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of a nucleotide that is generally at least about 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (such as glycosylation or phosphorylation). In one embodiment, the polypeptide is mesothelin polypeptide. A "residue" refers to an amino acid or amino acid mimetic incorporated in a polypeptide by an amide bond or amide bond mimetic. A polypeptide has an amino terminal (N-terminal) end and a carboxy terminal (C-terminal) end.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a tumor. "Ameliorating" refers to the reduction in the number or severity of signs or symptoms of a disease, such as cancer.

Promoter: A promoter is an array of nucleic acid control sequences that directs transcription of a nucleic acid. A promoter includes necessary nucleic acid sequences near the start site of transcription, for example, in the case of a polymerase II type promoter, a TATA element. A promoter also optionally includes distal enhancer or repressor elements which can be located as much as several thousand base pairs from the start site of transcription. Both constitutive and inducible promoters are included (see for example, Bitter et al., *Methods in Enzymology* 153:516-544, 1987).

Specific, non-limiting examples of promoters include promoters derived from the genome of mammalian cells (such as the metallothionein promoter) or from mammalian viruses (such as the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50%, such as at least 60%, at least 70%, at least 80%, at least 90%, at least 95%, or at least 98%, of the total peptide or protein content of the preparation.

The mesothelin polypeptides disclosed herein, or antibodies that specifically bind mesothelin, can be purified by any of the means known in the art. See for example *Guide to Protein Purification*, ed. Deutscher, *Meth. Enzymol.* 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques.

Recombinant toxins: Chimeric proteins in which a cell targeting moiety is fused to a toxin (Pastan et al., *Science,* 254:1173-1177, 1991). If the cell targeting moiety is the Fv portion of an antibody, the molecule is termed a recombinant immunotoxin (Chaudhary et al., *Nature,* 339:394-397, 1989). The toxin moiety is genetically altered so that it cannot bind to the toxin receptor present on most normal cells. Recombinant immunotoxins selectively kill cells which are recognized by the antigen binding domain. These recombinant toxins and immunotoxins can be used to treat cancer, for example, a cancer in which mesothelin is expressed.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a mesothelin polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus a mesothelin specific binding agent is an agent that binds substantially to a mesothelin polypeptide. In one embodiment, the specific binding agent is a human monoclonal antibody that specifically binds the mesothelin polypeptide.

The term "specifically binds" refers, with respect to an antigen such as mesothelin, to the preferential association of an antibody or other ligand, in whole or part, with a cell or tissue bearing that antigen and not to cells or tissues lacking that antigen. It is recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue bearing the mesothelin polypeptide as compared to a cell or tissue lacking the polypeptide. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Squamous cell carcinoma: A malignant neoplasm derived from stratified squamous epithelium, but which may also occur in sites such as bronchial mucosa where glandular or columnar epithelium is normally present. Squamous cell carcinoma is the most common type of skin cancer.

Subject: Living multi-cellular vertebrate organisms, a category that includes both human and veterinary subjects, including human and non-human mammals.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate a tumor. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Human Monoclonal Antibodies that Specifically Bind Mesothelin

Described herein are isolated human monoclonal antibodies specific for human mesothelin. The human monoclonal antibodies bind mesothelin with a dissociation constant ($K_d$) of about 25 nM or less. In some embodiments, the $K_d$ is about 24 nM, about 23 nM, about 22 nM, about 21 nM or about 20 nM or less. In other embodiments, the $K_d$ is about 15 nM or less, such as about 14 nM, about 13 nM, about 12 nM or about 11 nM. In other embodiments, the $K_d$ is about 10 nM or less, such as about 9 nM, about 8 nM, about 7 nM or about 6 nM. In other embodiments, the $K_d$ is about 5 nM or less, such as about 4 nM, about 3 nM, about 2.5 nM, about 2 nM or about 1 nM or less. In some embodiments, the $K_d$ is about 1 to about 20 nM, such as about 2.5 to about 15 nM, or about 5 to about 10 nM. Also described are compositions comprising the provided human monoclonal antibodies and a pharmaceutically acceptable carrier. Nucleic acids encoding these antibodies, expression vectors comprising these nucleic acids, and isolated host cells that express the nucleic acids are also provided.

Also described herein are immunoconjugates comprising the human monoclonal antibodies specific for human mesothelin. The immunoconjugates can comprise any therapeutic agent, toxin or other moiety. In one example, the toxin is PE or a variant or fragment thereof. Compositions comprising the immunoconjugates are also described.

Compositions comprising the human monoclonal antibodies specific for mesothelin can be used for research, diagnostic and/or therapeutic purposes. For example, the human monoclonal antibodies can be used to treat a subject diagnosed with cancer, such as a cancer that exhibits increased expression of mesothelin relative to normal cells. For example, the antibodies can be used to treat mesothelioma, pancreatic cancer, prostate cancer, ovarian cancer, lung cancer, stomach cancer or a squamous cell carcinoma Immunoconjugates comprising the mesothelin antibodies also can be used to treat a patient diagnosed with cancer. The human monoclonal antibodies can also be used to diagnose cancer in a subject. For example, the human monoclonal antibodies can be contacted with a sample from the patient, such as a blood sample, to detect elevated levels of mesothelin. The antibodies and compositions provided herein can also be used to detect cancer in a subject or to confirm the diagnosis of cancer in a patient. The antibodies can also be used to study the biology of mesothelin-expressing tumors.

Disclosed herein are fully human monoclonal antibodies that specifically bind human mesothelin. A major limitation in the clinical use of mouse monoclonal antibodies is the development of a human anti-murine antibody (HAMA) response in the patients receiving the treatments. The HAMA response can involve allergic reactions and an increased rate of clearance of the administered antibody from the serum. Various types of modified monoclonal antibodies have been developed to minimize the HAMA response while trying to maintain the antigen binding affinity of the parent monoclonal antibody. One type of modified monoclonal antibody is a human-mouse chimera in which a murine antigen-binding variable region is coupled to a human constant domain (Morrison and Schlom, *Important Advances in Oncology*, Rosenberg, S. A. (Ed.), 1989). A second type of modified monoclonal antibody is the complementarity determining region (CDR)-grafted, or humanized, monoclonal antibody (Winter and Harris, *Immunol. Today* 14:243-246, 1993). However, the antibodies disclosed herein are fully human; both the framework region and the CDRs are from human antibodies. Thus, a HAMA will not induced when these antibodies are administered to a human subject.

In one embodiment, the antibodies bind mesothelin with a dissociation constant ($K_d$) of about 25 nM or less. In several embodiments, the human monoclonal antibodies bind human mesothelin with a binding affinity of about 24 nM, about 23 nM, about 22 nM, about 21 nM about 20 nM, about 15 nM, about 10 nM, about 5 nM, about 2.5 nM or about 1 nM or less. In some embodiments, the human monoclonal antibodies disclosed herein also specifically bind mouse mesothelin.

In some embodiments, the human monoclonal antibody comprises at least a portion of the light chain amino acid sequence set forth as SEQ ID NO: 1. In some embodiments, the human monoclonal antibody comprises at least a portion of the heavy chain amino acid sequence set forth as SEQ ID NO: 2. In some examples, the portion of the light chain or heavy chain comprises one or more CDRs. In particular examples, the heavy chain of the antibody comprises amino acids 27-32 of SEQ ID NO: 1, amino acids 50-52 of SEQ ID NO: 1 or amino acids 89-98 of SEQ ID NO: 1, or a combination thereof; or the light chain of the antibody comprises amino acids 26-35 of SEQ ID NO: 2, amino acids 53-59 of SEQ ID NO: 2 or amino acids 98-109 of SEQ ID NO: 2, or a combination thereof; or both.

The monoclonal antibody can be of any isotype. The monoclonal antibody can be, for example, an IgM or an IgG antibody, such as $IgG_1$ or an $IgG_2$. The class of an antibody that specifically binds mesothelin can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds mesothelin that was originally IgM may be class switched to an IgG. Class switching can be used to convert one IgG subclass to another, such as from $IgG_1$ to $IgG_2$.

Fully human monoclonal antibodies include a human framework region. This human framework region can include the framework regions disclosed in one or both of SEQ ID NO: 1 or SEQ ID NO: 2 (these sequences include CDR sequences as well as framework sequences). However, the framework regions can be from another source. Additional examples of framework sequences that can be used include the amino acid framework sequences of the heavy and light chains disclosed in PCT Publication No. WO 2006/074071 (see, for example, SEQ ID NOs: 1-16).

Antibody fragments are encompassed by the present disclosure, such as Fab, $F(ab')_2$, and Fv which include a heavy chain and light chain variable region and are capable of binding the epitopic determinant on mesothelin. These antibody fragments retain the ability to selectively bind with the antigen. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

(6) A dimer of a single chain antibody ($scFV_2$), defined as a dimer of a scFV. This has also been termed a "miniantibody."

Methods of making these fragments are known in the art (see for example, Harlow and Lane, *Antibodies: A Laboratory Manual*, Cold Spring Harbor Laboratory, New York, 1988). In several examples, the variable region included in the antibody is the variable region of m912.

In a further group of embodiments, the antibodies are Fv antibodies, which are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242: 423, 1988; U.S. Pat. No. 4,946,778; Pack et al., *Bio/Technology* 11:1271, 1993; and Sandhu, supra). Dimers of a single chain antibody ($scFV_2$), are also contemplated.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology, Vol.* 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Additional recombinant anti-mesothelin human antibodies can be isolated by screening of a recombinant combinatorial antibody library, such as a Fab phage display library (see, for example, U.S. Patent Application Publication No. 2005/0123900). In some cases the phage display libraries are prepared using cDNAs of the variable regions of heavy and light chains prepared from mRNA derived from human lymphocytes. Methodologies for preparing and screening such libraries are known in the art. There are commercially available kits for generating phage display libraries (for example, the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; Fuchs et al., *Bio/Technology* 9:1370-1372, 1991; Hay et al., *Hum. Antibod. Hybridomas* 3:81-85, 1992; Huse et al., Science 246:1275-1281, 1989; McCafferty et al., *Nature* 348:552-554, 1990; Griffiths et al., *EMBO J.* 12:725-734, 1993)

In one embodiment, to isolate additional human antibodies that specifically bind mesothelin, a human antibody that specifically binds mesothelin, as described herein, is first used to select human heavy and light chain sequences having similar binding activity toward mesothelin, such as using the epitope imprinting methods disclosed in PCT Publication No. WO 93/06213. The antibody libraries used in this method are scFv libraries prepared and screened, using methods such as those as described in PCT Publication No. WO 92/01047, McCafferty et al., *Nature* 348:552-554, 1990; and/or Griffiths et al., *EMBO J.* 12:725-734, 1993 using human mesothelin as the antigen.

Once initial human variable light chain (VL) and variable heavy chain (VH) segments are selected, "mix and match" experiments, in which different pairs of the initially selected VL and VH segments are screened for mesothelin binding, are performed to select VL/VH pair combinations of interest. Additionally, to increase binding affinity of the antibody, the VL and VH segments can be randomly mutated, such as within H-CDR3 region or the L-CDR3 region, in a process analogous to the in vivo somatic mutation process responsible for affinity maturation of antibodies during a natural immune response. This in vitro affinity maturation can be accomplished by amplifying VH and VL regions using PCR primers complimentary to the H-CDR3 or L-CDR3, respectively. In this process, the primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be tested to determine the binding affinity for mesothelin.

Following screening and isolation of an antibody that binds mesothelin from a recombinant immunoglobulin display library, nucleic acid encoding the selected antibody can be recovered from the display package (for example, from the phage genome) and subcloned into other expression vectors by standard recombinant DNA techniques, as described herein. If desired, the nucleic acid can be further manipulated to create other antibody fragments, also as described herein. To express a recombinant human antibody isolated by screening of a combinatorial library, the DNA encoding the antibody is cloned into a recombinant expression vector and introduced into a mammalian host cells, as described herein.

IV. Immunoconjugates and Other Therapeutic Moieties

The human monoclonal antibodies specific for human mesothelin described herein can be conjugated to a therapeutic agent Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or Diphtheria toxin, encapsulating agents (such as liposomes) which themselves contain pharmacological compositions, radioactive agents such as $^{125}I$, $^{32}P$, $^{14}C$, $^{3}H$ and $^{35}S$ and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell. Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine ($—NH_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, label (such as enzymes or fluorescent molecules) drugs, toxins, and other agents to antibodies one skilled in the art will be able to determine a suitable method for attaching a given agent to an antibody or other polypeptide.

The antibodies or antibody fragments disclosed herein can be derivatized or linked to another molecule (such as another peptide or protein). In general, the antibodies or portion thereof is derivatized such that the binding to mesothelin is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company (Rockford, Ill.).

A human antibody that specifically binds mesothelin can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect mesothelin by x-ray, emission spectra, or other diagnostic techniques. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the mesothelin-specific human monoclonal antibodies described herein to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is *Pseudomonas* exotoxin (PE) (U.S. Pat. No. 5,602,095). As used herein "*Pseudomonas* exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989). In one embodiment, the cytotoxic fragment of PE retains at least 50%, at least 75%, at least 90%, or at lest 95% of the cytotoxicity of native PE. In some examples, the cytotoxic fragment is more toxic than native PE.

Native *Pseudomonas* exotoxin A (PE) is an extremely active monomeric protein (molecular weight 66 kD), secreted by *Pseudomonas aeruginosa*, which inhibits protein synthesis in eukaryotic cells. The method of PE action is inactivation of the ADP-ribosylation of elongation factor 2 (EF-2). The exotoxin contains three structural domains that act in concert to cause cytotoxicity. Domain 1a mediates cell binding. Domain II is responsible for translocation into the cytosol and domain III mediates ADP ribosylation of elongation factor 2. The function of domain Ib is unknown. PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; PCT Publication No. WO 99/51643; Pai et al., *Proc. Natl. Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

The mesothelin-specific antibodies described herein can also be used to target any number of different diagnostic or therapeutic compounds to cells expressing mesothelin on their surface. Thus, an antibody of the present disclosure can be attached directly or via a linker to a drug that is to be delivered directly to cells expressing cell-surface mesothelin. This can be done for therapeutic or research purposes. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-mesothelin antibody can be an encapsulation system, such as a liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^{3}H$, $^{125}I$, $^{35}S$, $^{14}C$, or $^{32}P$), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

V. Mesothelin Antibody Polynucleotides and Polypeptides

Nucleic acid molecules (also referred to as polynucleotides) encoding the polypeptides provided herein (including, but not limited to antibodies, immunoconjugates and fusion proteins) can readily be produced by one of skill in the art, using the amino acid sequences provided herein, sequences available in the art, and the genetic code. In addition, one of skill can readily construct a variety of clones containing functionally equivalent nucleic acids, such as nucleic acids which differ in sequence but which encode the same effector molecule or antibody sequence. Thus, nucleic acids encoding antibodies, conjugates and fusion proteins are provided herein. In some embodiments, the nucleotide sequence of the light chain of the mesothelin-specific human monoclonal antibody comprises SEQ ID NO: 6, or a portion thereof (such as a portion that encodes one or more CDRs). In some embodiments, the nucleotide sequence of the heavy chain of the mesothelin-specific human monoclonal antibody comprises SEQ ID NO: 7, or a portion thereof (such as a portion that encodes one or more CDRs).

Nucleic acid sequences encoding the human antibodies that specifically bind mesothelin can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding human antibodies that specifically bind mesothelin can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids encoding native EM or anti-mesothelin antibodies can be modified to form the EM, antibodies, or immunoconjugates of the present disclosure. Modification by site-directed mutagenesis is well known in the art. Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one embodiment, immunoconjugates are prepared by inserting the cDNA which encodes a human mesothelin-specific monoclonal antibody into a vector which comprises the cDNA encoding the EM. The insertion is made so that the antibody and the EM are read in frame, that is in one continuous polypeptide which contains a functional antibody region and a functional EM region. In one embodiment, cDNA encoding an EM, label or enzyme is ligated to an antibody so that the EM, label or enzyme is located at the carboxyl terminus of the antibody. In another embodiment, the EM, label or enzyme is located at the amino terminus of the antibody. In a another example, cDNA encoding the EM, label or enzyme is ligated to a heavy chain variable region of an antibody, so that the EM, label or enzyme is located at the carboxyl terminus of the heavy chain variable region. The heavy chain-variable region can subsequently be ligated to a light chain variable region of the antibody using disulfide bonds. In a yet another example, cDNA encoding an EM, label or enzyme is ligated to a light chain variable region of an antibody, so that the EM, label or enzyme is located at the carboxyl terminus of the light chain variable region. The light chain-variable region can subsequently be ligated to a heavy chain variable region of the antibody using disulfide bonds.

Once the nucleic acids encoding an EM, anti-mesothelin antibody, or an immunoconjugate are isolated and cloned, the desired protein can be expressed in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines.

One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

The expression of nucleic acids encoding the isolated proteins described herein can be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, maintenance of the correct reading frame of that gene to permit proper translation of mRNA, and stop codons.

To obtain high level expression of a cloned gene, it is desirable to construct expression cassettes which contain, at the minimum, a strong promoter to direct transcription, a ribosome binding site for translational initiation, and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, SV40 or cytomegalovirus, and a polyadenylation sequence, and can further include splice donor and acceptor sequences. The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Modifications can be made to a nucleic acid encoding a polypeptide described herein (i.e., a human mesothelin-specific monoclonal antibody or an immunoconjugate comprising the antibody) without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the recombinant immunoconjugates, antibodies, and/or effector molecules can be purified according to standard procedures of the art, including ammonium sulfate precipitation, affinity columns, column chromatography, and the like (see, generally, R. Scopes, PROTEIN PURIFICATION, Springer-Verlag, N.Y., 1982). The antibodies, immunoconjugates and effector molecules need not be 100% pure. Once purified, partially or to homogeneity as desired, if to be used therapeutically, the polypeptides should be substantially free of endotoxin.

Methods for expression of antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5-fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis, 2nd ed*., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

VI. Compositions and Therapeutic Methods

Compositions are provided that include one or more of the antibodies that specifically bind mesothelin that are disclosed herein in a carrier. Compositions comprising immunoconjugates or immunotoxins are also provided. The compositions can be prepared in unit dosage forms for administration to a subject. The amount and timing of administration are at the discretion of the treating physician to achieve the desired purposes. The antibody can be formulated for systemic or local (such as intra-tumor) administration. In one example, the antibody that specifically binds mesothelin is formulated for parenteral administration, such as intravenous administration.

The compositions for administration can include a solution of the antibody that specifically binds mesothelin dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science,* 19th ed., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

The antibody that specifically binds mesothelin can be administered to slow or inhibit the growth of cells, such as cancer cells. In these applications, a therapeutically effective amount of an antibody is administered to a subject in an amount sufficient to inhibit growth, replication or metastasis of cancer cells, or to inhibit a sign or a symptom of the cancer. Suitable subjects may include those diagnosed with a cancer that expresses mesothelin, such as, but not limited to, a mesothelioma, stomach cancer, squamous cell carcinomas, prostate cancer, lung cancer, pancreatic cancer or ovarian cancer.

A therapeutically effective amount of a human mesothelin-specific antibody will depend upon the severity of the disease and the general state of the patient's health. A therapeutically effective amount of the antibody is that which provides either subjective relief of a symptom(s) or an objectively identifiable improvement as noted by the clinician or other qualified observer. These compositions can be administered in conjunction with another chemotherapeutic agent, either simultaneously or sequentially.

Many chemotherapeutic agents are presently known in the art. In one embodiment, the chemotherapeutic agents is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of the invention. Examples of useful COX-II inhibitors include CELEBREX™ (alecoxib), valdecoxib, and rofecoxib. Examples of useful matrix metalloproteinase inhibitors are described in PCT Publication No. WO 96/33172 (published Oct. 24, 1996), PCT Publication No. WO 96/27583 (published Mar. 7, 1996), European Patent Application No. 97304971.1 (filed Jul. 8, 1997), European Patent Application No. 99308617.2 (filed Oct. 29, 1999), PCT Publication No. WO 98/07697 (published Feb. 26, 1998), PCT Publication No WO 98/03516 (published Jan. 29, 1998), PCT Publication No WO 98/34918 (published Aug. 13, 1998), PCT Publication No WO 98/34915 (published Aug. 13, 1998), PCT Publication No WO 98/33768 (published Aug. 6, 1998), PCT Publication No WO 98/30566 (published Jul. 16, 1998), European Patent Publication 606,046 (published Jul. 13, 1994), European Patent Publication 931,788 (published Jul. 28, 1999), PCT Publication No WO 90/05719 (published May 31, 1990), PCT Publication No WO 99/52910 (published Oct. 21, 1999), PCT Publication No WO 99/52889 (published Oct. 21, 1999), PCT Publication No WO 99/29667 (published Jun. 17, 1999), PCT International Application No. PCT/IB98/01113 (filed Jul. 21, 1998), European Patent Application No. 99302232.1 (filed Mar. 25, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997). In one example, the MMP inhibitors do not induce arthralgia upon administration. In another example, the MMP inhibitor selectively inhibits MMP-2 and/or MMP-9 relative to the other matrix-metalloproteinases (such as MMP-1, MMP-3, MMP-4, MMP-5, MMP-6, MMP-7, MMP-8, MMP-10, MMP-11, MMP-12, and MMP-13). Some specific examples of MMP inhibitors of use are AG-3340, RO 32-3555, RS 13-0830, 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxabicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

The antibodies that specifically bind mesothelin can also be used with signal transduction inhibitors, such as agents that can inhibit EGF-R (epidermal growth factor receptor) responses, such as EGF-R antibodies, EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc.). EGF-R inhibitors are described in, for example in PCT Publication Nos. WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents also include, but are not limited to, the monoclonal antibodies C225 and anti-EGFR 22Mab (ImClone Systems Incorporated), ABX-EGF (Abgenix/Cell Genesys), EMD-7200 (Merck KgaA), EMD-5590 (Merck KgaA), MDX-447/H-477 (Medarex Inc. and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), CI-1033 (Warner Lambert Parke Davis), CI-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co.), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGF-R Vaccine (York Medical/Centro de Immunologia Molecular (CIM)).

VEGF inhibitors, for example SU-5416 and SU-6668 (Sugen Inc.), SH-268 (Schering), and NX-1838 (NeXstar) can also be used in conjunction with an antibody that specifically binds mesothelin. VEGF inhibitors are described in, for example in PCT Publication No. WO 99/24440 (published May 20, 1999), PCT International Application PCT/IB99/00797 (filed May 3, 1999), PCT Publication No. WO 95/21613 (published Aug. 17, 1995), PCT Publication No. WO 99/61422 (published Dec. 2, 1999), U.S. Pat. No. 5,834,504 (issued Nov. 10, 1998), PCT Publication No. WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), PCT Publication No. WO 99/10349 (published Mar. 4, 1999), PCT Publication No. WO 97/32856 (published Sep. 12, 1997), PCT Publication No. WO 97/22596 (published Jun. 26, 1997), PCT Publication No. WO 98/54093 (published Dec. 3, 1998), PCT Publication No. WO 98/02438 (published Jan. 22, 1998), WO 99/16755 (published Apr. 8, 1999), and PCT Publication No. WO 98/02437 (published Jan. 22, 1998). Other examples of some specific VEGF inhibitors are IM862 (Cytran Inc.); anti-VEGF monoclonal antibody of Genentech, Inc.; and angiozyme, a synthetic ribozyme from Ribozyme and Chiron. These and other VEGF inhibitors can be used in conjunction with an antibody that specifically binds mesothelin.

ErbB2 receptor inhibitors, such as GW-282974 (Glaxo Wellcome pic), and the monoclonal antibodies AR-209 (Aronex Pharmaceuticals Inc.) and 2B-1 (Chiron), can furthermore be combined with the compound of the invention, for example those indicated in PCT Publication No. WO 98/02434 (published Jan. 22, 1998), PCT Publication No. WO 99/35146 (published Jul. 15, 1999), PCT Publication No. WO 99/35132 (published Jul. 15, 1999), PCT Publication No. WO 98/02437 (published Jan. 22, 1998), PCT Publication No. WO 97/13760 (published Apr. 17, 1997), PCT Publication No. WO 95/19970 (published Jul. 27, 1995), U.S. Pat. No. 5,587,458 (issued Dec. 24, 1996), and U.S. Pat. No. 5,877,305 (issued Mar. 2, 1999). ErbB2 receptor inhibitors of use are also described in U.S. Provisional Application No. 60/117,341, filed Jan. 27, 1999, and in U.S. Provisional Application No. 60/117,346, filed Jan. 27, 1999.

Single or multiple administrations of the compositions are administered depending on the dosage and frequency as required and tolerated by the patient. In any event, the composition should provide a sufficient quantity of at least one of the antibodies disclosed herein to effectively treat the patient. The dosage can be administered once but may be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core.

In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

VI. Diagnostic Methods and Kits

A method is provided herein for the detection of the expression of mesothelin in vitro or in vivo. In one example, expression of mesothelin is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a rat, mouse, cow, dog, guinea pig, rabbit, or primate. In one embodiment, the primate is macaque, chimpanzee, or a human.

In several embodiments, a method is provided for detecting a malignancy such as a mesothelioma, stomach cancer, squamous cell carcinomas, prostate cancer, lung cancer, or ovarian cancer. Blood samples from patients with mesothelin-positive cancers contain detectable amounts of secreted mesothelin protein. Thus, mesothelin-specific antibodies can be used to detect mesothelin in a blood sample from a subject to detect cancer in the subject, or confirm a diagnosis of cancer in a subject.

The invention provides a method for detecting mesothelin in a biological sample, wherein the method includes contacting a biological sample with a human antibody that binds mesothelin under conditions conducive to the formation of an immune complex, and detecting the immune complex, to detect the mesothelin in the biological sample. In one example, the detection of mesothelin in the sample indicates that the subject has a malignancy. In another example, the detection of mesothelin in the sample indicates that the subject is prone to metastasis. In another example, detection of mesothelin in the sample confirms a diagnosis of cancer in a subject.

In one embodiment, the human antibody that specifically binds mesothelin is directly labeled with a detectable label. In another embodiment, the human antibody that specifically binds mesothelin (the first antibody) is unlabeled and a second antibody or other molecule that can bind the human antibody that specifically binds mesothelin is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^{3}H$.

In an alternative embodiment, mesothelin can be assayed in a biological sample by a competition immunoassay utilizing mesothelin standards labeled with a detectable substance and an unlabeled human antibody that specifically binds mesothelin. In this assay, the biological sample, the labeled mesothelin standards and the human antibody that specifically bind mesothelin are combined and the amount of labeled mesothelin standard bound to the unlabeled antibody is determined. The amount of mesothelin in the biological sample is inversely proportional to the amount of labeled mesothelin standard bound to the antibody that specifically binds mesothelin.

The immunoassays and method disclosed herein can be used for a number of purposes. In one embodiment, the human antibody that specifically binds mesothelin may be used to detect the production of mesothelin in cells in cell culture. In another embodiment, the antibody can be used to detect the amount of mesothelin in a biological sample. Increased expression of mesothelin is associated with several types of cancer, including mesotheliomas, stomach cancer, squamous cell carcinomas, prostate cancer, lung cancer and ovarian cancer. In one embodiment, a kit is provided for detecting mesothelin in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of soluble mesothelin protein. Kits for detecting a polypeptide will typically comprise a human antibody that specifically binds mesothelin, such as any of the antibodies disclosed herein. In some embodiments, an antibody fragment, such as an Fv fragment or a Fab is included in the kit. In a further embodiment, the antibody is labeled (for example, with a fluorescent, radioactive, or an enzymatic label).

In one embodiment, a kit includes instructional materials disclosing means of use of an antibody that specifically binds mesothelin. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting mesothelin in a biological sample generally includes the steps of contacting the biological sample with an antibody which specifically reacts, under immunologically reactive conditions, to a mesothelin polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), enzyme linked immunosorbent assays (ELISA), or immunohistochemical assays. The antibodies can also be used for fluorescence activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620). Any of the human antibodies that specifically bind mesothelin, as disclosed herein, can be used in these assays. Thus, the antibodies can be used in a conventional immunoassay, including, without limitation, an ELISA, an RIA, FACS, tissue immunohistochemistry, Western blot or immunoprecipitation.

The following examples are provided to illustrate certain particular features and/or embodiments. These examples should not be construed to limit the disclosure to the particular features or embodiments described.

EXAMPLES

Example 1

Identification and Characterization of a Fully Human Monoclonal Mesothelin-Specific Antibody Materials and Methods Cell Cultures A431 cells, human epidermoid carcinoma cells, were maintained in RPMI1640
supplemented with 10% FBS and penicillin/streptomycin (complete growth medium).
A431 cells do not express mesothelin. H9 cells are stable clone cells established from
A431 cells that were transfected with a vector carrying full-length mesothelin cDNA. H9 cells were maintained in complete RPMI1640 growth medium supplemented
with 0.75 mg/ml G418. OVCAR-3 cells were purchased from ATCC (Manassas, Va.) and maintained in RPMI1640 complete growth medium.

Expression of Recombinant Mesothelin Protein

A fragment consisting of amino acids 296-600 of human mesothelin (Genbank Accession No. AY743922; SEQ ID NO: 4) was cloned from pcDNA3.2 to baculovirus transfer vector pAcGP67 (BD Biosciences Pharmingen) via Sma I and Nod sites. The recombinant product contained the amino acid sequence ADPG (SEQ ID NO: 5) on the N-terminus and $His_6$ on the C-terminus. The product was co-transfected with BaculoGold™ viral DNA into SF9 insect cells according to manufacturer's instructions. Mesothelin protein was purified from conditioned medium with a nickel-chelating column, and further polished with a Superdex™ 75 gel filtration column in PBS. The purity of recombinant mesothelin was evaluated by SDS-PAGE.

Antibody Selection by Phage Display

Purified mesothelin was labeled with biotin and used as bait to screen a human naïve Fab phage library. Briefly, amplified phage (approximately $10^{12}$ PFU) pre-absorbed with MyOne™ Streptavidin T1 beads (Invitrogen, Carlsbad, Calif.) was incubated with 4 μg of biotin-mesothelin for 2 hours. Specific phages were captured by fresh streptavidin beads. After extensive washing of the beads with PBS+0.05% Tween 20, phage was rescued by exponentially growing TG1 bacteria and helper phage. Pannings were repeated three times with more stringent washes during the last two rounds. Three hundred colonies were picked from the last two rounds of panning and rescued with helper phage for screening. Two unique clones were selected, of which clone m912 had the highest affinity.

Antibody Expression and Purification

The Fab fragment was expressed in *E. coli* HB2151 cells (Feng et al., *Mol. Cancer. Ther.* 5:114-120, 2006). A single chain form of m912 was made by cloning VH and VL from Fab, connected by linker 3 (GGGGS; SEQ ID NO: 8), into pComb3x (Scott et al., "Phage-display vector," In. Phage display: a laboratory manual. Cold Spring Harbor, N.Y.: Cold Spring Harbor Laboratory Press, Barbas, C F, III, editor, 2001). Expression and purification of scFv were similar to that of the Fab. Fab was converted into IgG1 by subcloning the heavy chain variable region and light chain into pDR12. 293 Free Style™ cells were transfected with pDR12-m912, and IgG was secreted into the medium. Fab and IgG were purified with a protein G column, and scFv was purified with a nickel-chelating column. All preparations were dialyzed against PBS.

ELISA Binding Assay

Antigen (mesothelin) diluted in PBS was coated on narrow-well 96-well plates at 50 ng/well overnight at 4° C. Wells were blocked with 100 μl of 4% milk/PBS (MPBS) for 1 hour at 37° C. For Fab binding kinetics, Fab was titrated from 3000 nM to 0.038 nM (1:5 serial dilutions). Fifty μl of diluted Fab was added to duplicate wells. For competition ELISA, designated concentrations of competing IgG were included in all Fab solutions. After 2 hours of incubation at 37° C., the wells were washed with PBST (PBS+0.05% Tween 20) 4 times. Bound Fab was detected with anti-FLAG-HRP mAb (1:1000) (Sigma) for 1 hour at 37° C. Wells were washed again with PBST. Substrate ABTS was added (50 μl/well), and the reaction was read at A405 nm. For ELISA with IgG, a goat anti-human Fc IgG conjugated with HRP was used at 1:1000.

Flow Cytometry

A413 cells and H9 cells were detached with cell dissociation buffer and rinsed in PBS. Aliquots of cells were incubated with primary antibody (m912, or isotype controls) at the indicated concentrations in 250 μl of RPMI+10% FBS for 1 hour on ice. Unbound antibodies were washed away with medium. Secondary antibody goat anti-human IgG conjugated with FITC (Sigma) was incubated with cells at 8 μl/ml for 30 minutes. For detection of Fab or scFv, 1.6 μg/ml of anti-$His_6$ monoclonal antibody (Qiagen) and 8 μl/ml of goat anti-mouse IgG-FITC (Sigma) were incubated with cells. Cells were washed and resuspended in PBS+0.5% BSA for flow cytometry on FACSCalibur™ (Beckton Dickinson).

ADCC (Antibody-Dependent Cell-Mediated Cytotoxicity)

Peripheral blood mononuclear cells (PBMC) were isolated from blood of healthy donors with Ficoll-Paque™ Plus (GE Healthcare). The viability of isolated cells was greater than 95%. PBMC were seeded in 96-well plates in RPMI+10% FBS at 500,000 cells/well. Cells were incubated at 37° C. and allowed to attach to the plates for 3 hours. Unattached cells were rinsed off by two washes of warm PBS. Cells adhered to the plate were used as the effector cells. Target cells, either A431 or H-9 cells, were trypsinized and resuspended into single-cell suspensions. The target cells were incubated with various concentrations of antibody at room temperature for 30 minutes then added to effector cells at 10,000 cells/well. The ratio of effector and target cells was 50:1. The plate was centrifuged at 300×g for 5 minutes and incubated at 37° C. for 24 hours. Supernatant (100 μl) was transferred to an all white plate and 100 μl of CytoTox-ONE™ reagent (Promega) was added to each well. The lactate dehydrogenase (LDH) from lysed cells converts CytoTox substrate to fluorescent resazurin, which was measured in a fluorometer (Ex 560 nm/Em 590 nm). The specific lysis percentage was calculated as follows: (experimental treatment-effector cell control)/(high control-target cell control)×100%. Target cells alone treated with 1% Triton X-100 were used as high control. Each treatment was repeated in 6 duplicate wells. Each assay plate included control wells.

Western Blot

H9 and OVCAR-3 cells were lysed in RIPA buffer (50 mM Tris, pH 7.4, 1% Triton X-100, 0.1% SDS, 1% deoxycholate, 150 mM NaCl, 5 mM NaF, 5 mM EDTA). After centrifugation at 20,000×g for 20 minutes, the clear supernatant was resolved on 4-12% NuPAGE™ and transferred to PVDF membrane. Primary antibodies used for blotting were MORAb-009 at 0.5 μg/ml (for mesothelin) and goat polyclonal antibody against actin (clone 1-19, Santa Cruz Biotechnology, for monitoring equal loading) at 1 μg/ml, respectively. Corresponding secondary antibodies were goat anti-human Fc-HRP and donkey anti-goat IgG-HRP at 1 μg/ml for detection.

Results

Expression and Purification of Recombinant Human Mesothelin in Insect Cells

To efficiently select antibodies from phage libraries, purified recombinant antigen, in this case mesothelin, is needed. In order to include as much as possible of the mesothelin molecule, its entire extracellular domain, including the GPI linkage site serine-598 was expressed (Hassan et al., *Clin. Cancer Res.* 10:3937-3942, 2004). To achieve relatively high yields and glycosylation in eukaryotic cells, mesothelin was cloned in a baculovirus expression vector. The transfer vector pAcGP67 has a signal peptide that directs secretion of recombinant protein into medium. Indeed, recombinant mesothelin (amino acids 296-600; numbered with reference to SEQ ID NO: 4) expressed in SF9 insect cells was secreted into the culture medium. The mesothelin purified by a two-step procedure was greater than 95% in purity and migrated at approximately 35 kD (FIG. 1A) on a polyacrylamide gel. It migrated slightly faster than the same fragment that was expressed in mammalian cells, reflecting differences in post-translational modifications, such as glycosylation. The purified mesothelin was recognized by MORAb-009 (Chowdhury et al., *Proc. Natl. Acad. Sci. USA* 95:669-674, 1998), a mouse/human chimeric IgG, and was used for panning of a naïve human Fab phage display library.

High-Affinity Binding of m912 to Recombinant Mesothelin

Mesothelin produced in insect cells was labeled with biotin and used for panning of the large naïve Fab library as described above. After the third and fourth rounds of panning, three hundred clones were screened and two positive clones with different sequences were identified. Clone m912 bound with higher affinity to mesothelin than the other clone and was selected for further characterization. The light (SEQ ID NO: 1) and heavy (SEQ ID NO: 2) chain amino acid sequences of m912 are shown below. The corresponding nucleotide sequences of the heavy and light chains are set forth herein as SEQ ID NO: 6 and SEQ ID NO: 7, respectively.

m912 light chain (CDR1, CDR2 and CDR3 are shown in bold):

(SEQ ID NO: 1)

DIQMTQSPSSLSASVGDRVTITCRASQSISSYLNWYQQKPGKAPKLLI

YAASSLQSGVPSGFSGSGSGTDFTLTISSLQPEDFATYYCQQSYSTPL

TFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC m912 heavy chain (CDR1, CDR2 and CDR3 are shown in bold):

(SEQ ID NO: 2)

QVQLQESGPGLVKPSETLSLTCTVSGGSVSSGSYYWSWIRQPPGKGLE

WIGYIYYSGSTNYNPSLKSRVTISVDTSKNQFSLKLSSVTAADTAVYY

CAREGKNGAFDIWGQGTMVTVSSASTKGPSVFPLAPSSKSTSGGTAAL

GCLVKDYFPEPVTVSWNSGALTSGVHTFPAVLQSSGLYSLSSVVTVPS

SSLGTQTYICNVNHKPSNTKVDKKVEPKSCDKTSGQAG

Figure 1B:
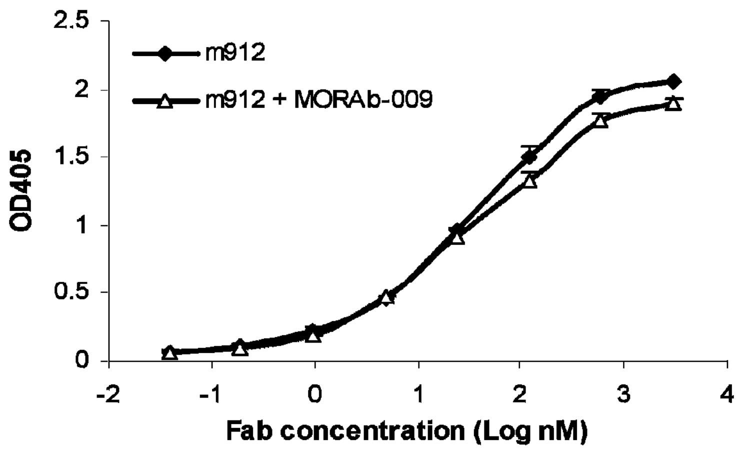
FIGS. 1B-1D are graphs showing high affinity binding of Fab m912 and IgG1 m912 to recombinant mesothelin. (B) Binding of Fab m912 to recombinant mesothelin coated on an ELISA plate (-♦-). For competition ELISA, 3 nM MORAb-009 was added to all Fab m912 solutions (-Δ-). (C) Binding of IgG1 m912 to recombinant mesothelin by ELISA. (D) Binding of Fab m912 to mouse recombinant mesothelin by ELISA.
Figure 1C:
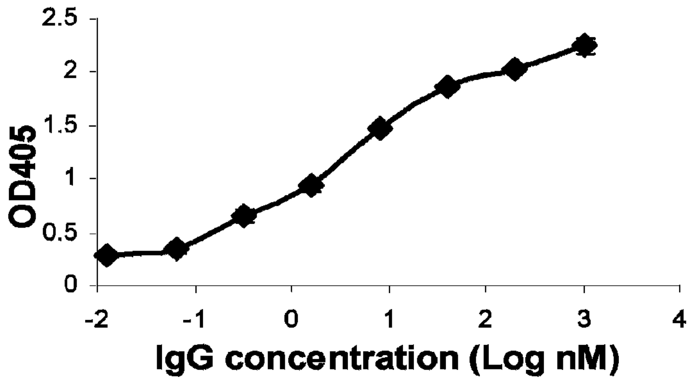
Figure 1D:
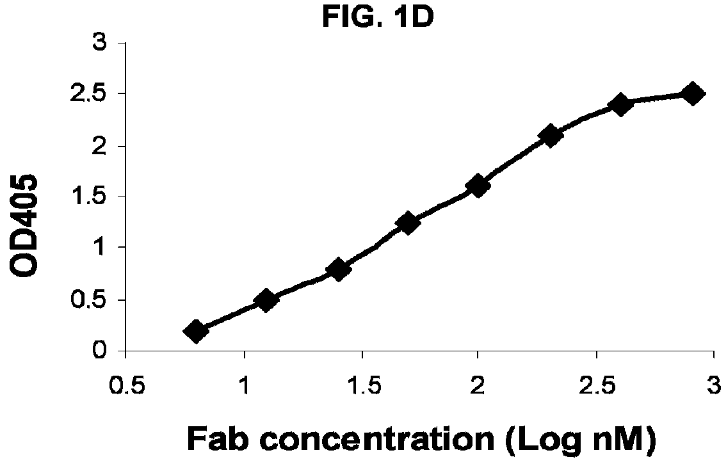

Fab m912 was converted to single chain and IgG1 formats. Fab m912 bound to mesothelin with an $EC_{50}$ of 20 nM as measured by ELISA (FIG. 1B). Inclusion of MORAb-009 at a concentration higher than its $EC_{50}$ in Fab m912 ELISA did not reduce binding signals, suggesting that the two antibodies have different epitopes on mesothelin (FIG. 1B). The IgG1 exhibited a higher effective binding affinity (avidity) of approximately 1.5 nM as measured by ELISA (FIG. 1C). Deglycosylation of mesothelin by PNGase F reduced its size by at least 3 kD, but it did not change the binding ability of m912, indicating that the m912 epitope is independent of mesothelin glycosylation. Fab m912 also recognized mouse mesothelin with about the same affinity (FIG. 1D).

Specific Binding of m912 to Cell Surface-Associated Mesothelin

It is essential that a therapeutic or diagnostic antibody recognize the native protein.

Figure 2A:
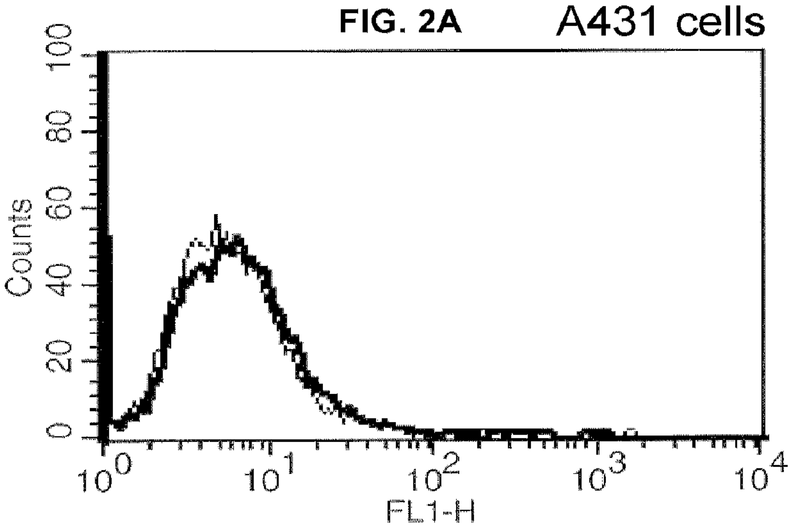
FIGS. 2A-2C are FACS plots showing specific, high-affinity binding of Fab m912 and scFv m912 to cell surface-associated mesothelin. (A) Lack of Fab m912 binding to mesothelin-negative (A431) cells. (B) Binding of Fab m912, but not of a control Fab to mesothelin-positive H9 cells. (C) Binding of scFv m912, but not of a control scFv to mesothelin-positive H9 cells. In all three panels, thick lines represent binding of m912 in Fab or scFv formats and thin lines are for control Fab and scFv. The concentrations of all Fabs and scFvs used in these studies were 40 nM and 100 nM, respectively.
Figure 2B:
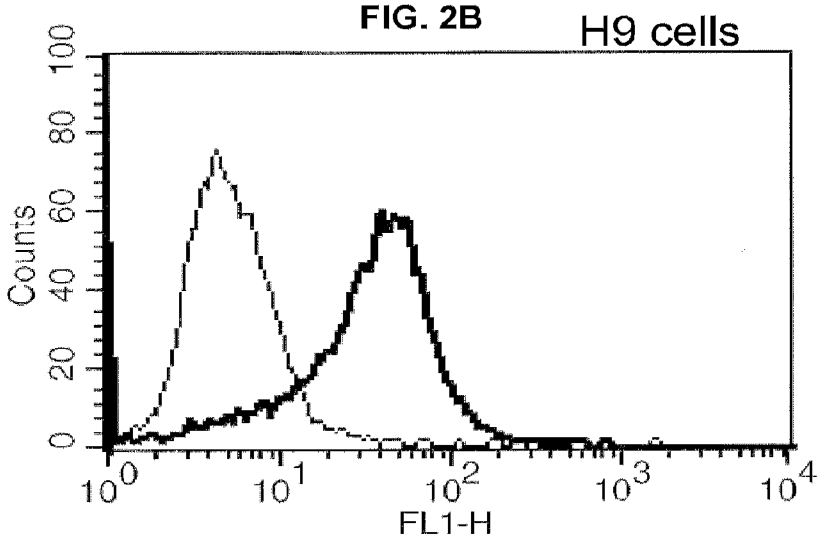
Figure 2C:
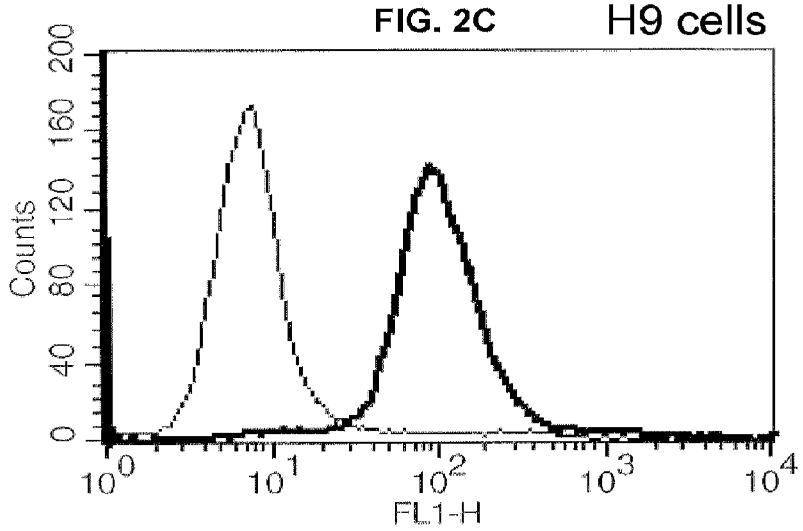
Figure 3A:
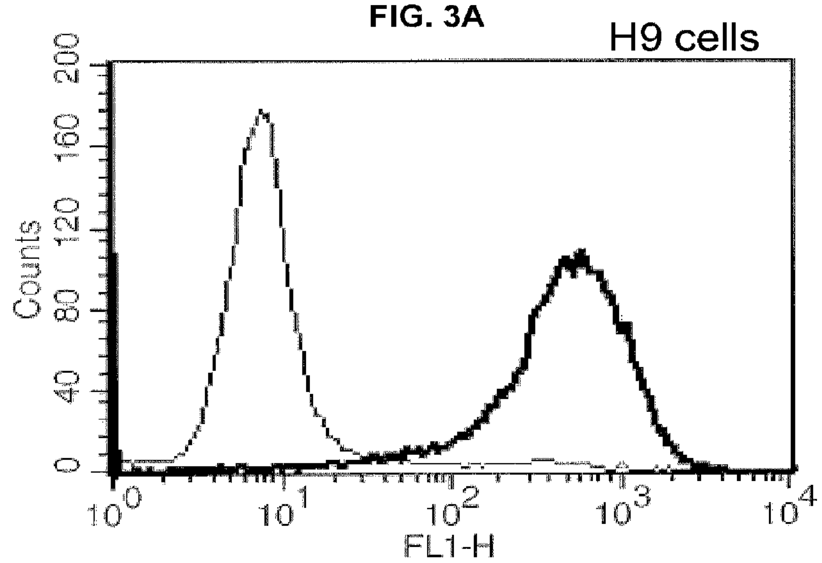
FIGS. 3A-3C are graphs showing high avidity binding of IgG1 m912 to cell surface-associated mesothelin. (A) IgG1 m912 at 5 nM was incubated with mesothelin-positive H9 cells, the cells were washed and further incubated with goat anti-human IgG conjugated with FITC, then washed and analyzed by flow cytometry. An isotype control IgG (thin line) at 100 nM was used as negative control. (B) The same flow cytometry analyses were performed at different concentrations of IgG1 m912, and medium fluorescent units plotted as function of the antibody concentration. (C) IgG1 m912 at 625 nM (thin line without shade) and 3125 nM (thick line) was incubated with OVCAR-3 cancer cells, as performed similarly in FIG. 3A. MORAb-009 was used at 100 nM (dotted line). An isotype control human IgG was used at 625 nM (thin line, shaded area).

Therefore, Fab m912 was tested for binding to native mesothelin associated with cell surfaces. H9 cells, which stably express mesothelin protein, were used. Fab m912 bound to H9 cells but not to A431 cells (FIG. 2B), indicating that it is highly specific and does not recognize other membrane proteins on these cells. Various clinical applications require different sizes and valences of antibodies for best effect. For example, small sizes are preferred for targeting and imaging, whereas full-size antibodies (IgGs) have much longer half-life in circulation, and some are able to mediate effecter functions. Therefore, Fab m912 was converted to scFv and IgG formats, and tested for binding to cells by flow cytometry. It was found that m912 in both formats, scFv and IgG1, can bind specifically to cell surface-associated mesothelin (FIGS. 2C and 3A).

Figure 3B:
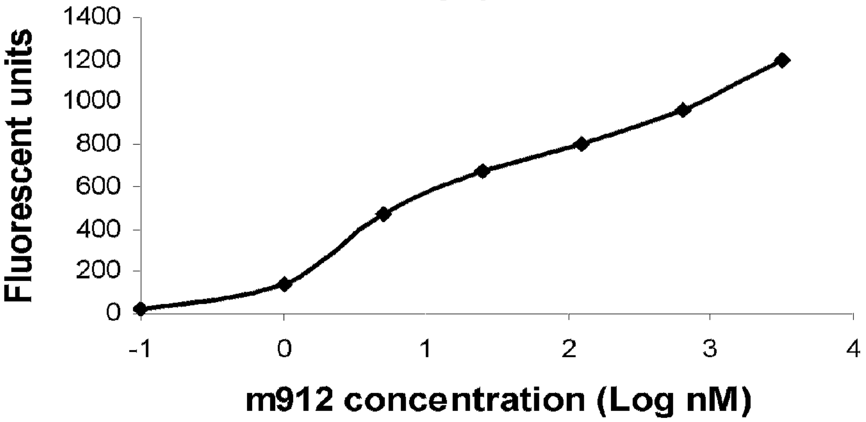
Figure 3C:
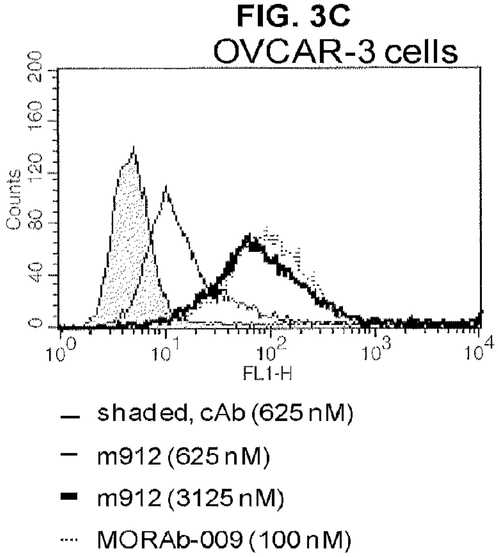
Figure 3D:
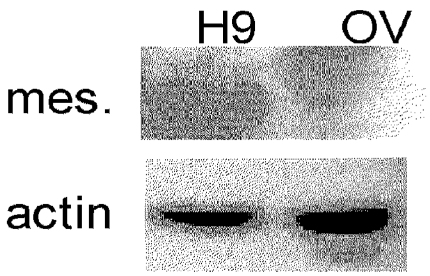
FIG. 3D is a digital image of a Western blot for mesothelin protein. Levels of mesothelin proteins in H9 and OVCAR-3 cells were detected by Western blot. Equal amount of lysates were loaded as shown by actin blot.

To estimate the binding ability (avidity) of IgG1 m912 to native cell surface-associated mesothelin, antibody concentrations ranging from 0.1 nM to 3125 nM and H9 cells were used in a flow cytometry experiment (FIG. 3B). Even at the lowest concentration of 0.1 nM, IgG m912 exhibited significant binding to H9 cells. Based on the medium fluorescent units bound to H9 cells at each m912 concentration, a 50% binding of m912 was estimated to be at about 5-10 nM for these cells. The binding of m912 was further tested in non-transfected cancer cells, ovarian cancer cell line, OVCAR-3. These cells have been reported to be positive with cell surface mesothelin. In flow cytometry, m912 showed specific binding in a dose-dependent fashion (FIG. 3C); however, higher concentrations were required to reach the same level of binding seen with H9 cells. This was partially due to the much lower levels of mesothelin protein expressed by the OVCAR-3 cells than by H9 cells as demonstrated by Western blot (FIG. 3D). MORAb-009 still showed high avidity on OVCAR-3 cells.

Specific Lysis of Mesothelin-Positive Cells by m912 in Presence of PBMC

Figure 4:
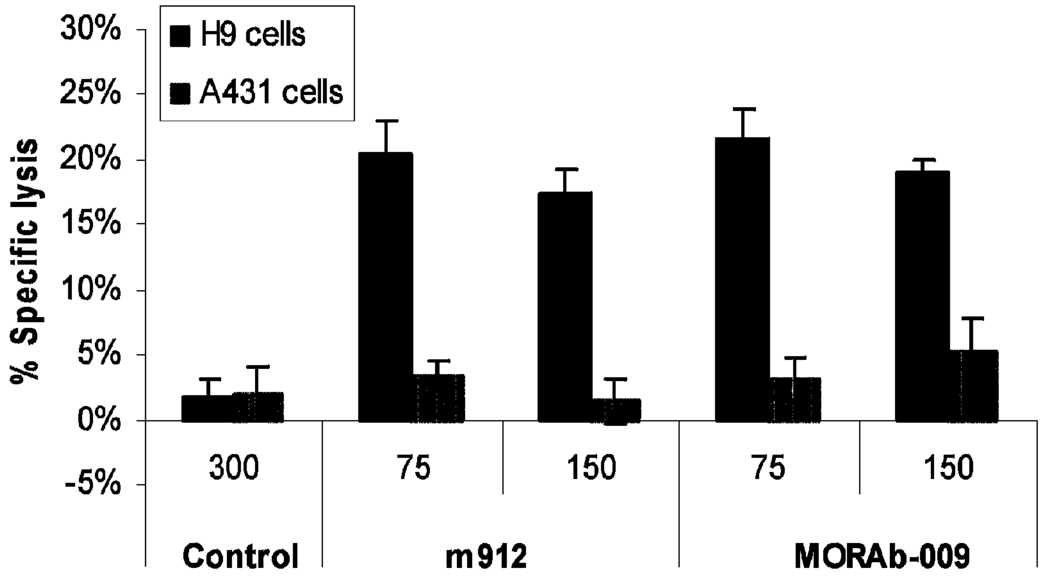
FIG. 4 is a bar graph showing IgG1 m912 induced ADCC in mesothelin-positive cells, but not in mesothelin-negative cells. Freshly isolated PBMCs were incubated with target cells (H9 or A431 cells) at a ratio of 50:1, in the presence of IgG1 m912 or MORAb-009 at two different concentrations (75 or 150 nM), or an isotype control IgG1 at 300 nM. ADCC was detected with CytoTox-ONE™ reagent, which measures the lactate dehydrogenase released by lysed target cells. The percentage (%) of specific lysis was calculated as described in Example 1 below.

Therapeutic antibodies can kill cancer cells via ADCC mediated by the Fc portion of IgG. To test whether IgG1 m912 has such activity, a cell growth assay based on A431 and H9 cells was used. Incubation of IgG1 m912 alone with these cells did not affect their growth. However, in the presence of PBMCs isolated from peripheral blood of healthy donors, IgG1 m912 specifically lysed mesothelin-positive (H9) cells likely by ADCC but not mesothelin-negative (A431) cells. The mouse-human chimeric anti-mesothelin antibody MORAb-009 (Hassan et al., *Cancer Immunol.* 7:20, 2007) used as a positive control exhibited similar activity, while a control isotype antibody had a baseline lysis activity (FIG. 4). These results indicate that IgG1 m912 lysed the H9 cells by ADCC through specific binding to cell surface-associated mesothelin. Thus, m912 has the potential to kill mesothelin-positive tumor cells in vivo.

Example 2

Mesothelin-Specific Monoclonal Antibodies for Detecting Cancer in a Subject or Confirming the Diagnosis of Cancer in a Subject This example describes the use of mesothelin-specific human monoclonal antibodies for the detection of cancer in a subject. This example further describes the use of these antibodies to confirm the diagnosis of cancer in a subject.

A blood sample is obtained from the patient diagnosed with, or suspected of having a mesothelin-positive cancer (i.e., a cancer that overexpresses mesothelin, such as mesothelioma, prostate cancer, lung cancer, stomach cancer, squamous cell carcinoma, pancreatic cancer or ovarian cancer). A blood sample taken from a patient that does not have cancer is used as a control. An ELISA is performed to detect the presence of soluble mesothelin in the blood sample. Proteins present in the blood samples (the patient sample and control sample) are immobilized on a solid support, such as a 96-well plate, according to methods well known in the art (see, for example, Robinson et al., *Lancet* 362:1612-1616, 2003). Following immobilization, mesothelin-specific monoclonal antibody directly labeled with a fluorescent marker is applied to the protein-immobilized plate. The plate is washed in an appropriate buffer, such as PBS, to remove any unbound antibody and to minimize non-specific binding of antibody. Fluorescence can be detected using a fluorometric plate reader according to standard methods. An increase in fluorescence intensity of the patient sample, relative to the control sample, indicates the anti-mesothelin antibody specifically bound proteins from the blood sample, thus detecting the presence of mesothelin protein in the sample. Detection of mesothelin protein in the patient sample indicates the patient has a mesothelin-positive cancer, or confirms diagnosis of cancer in the subject.

Example 3

Mesothelin-Specific Monoclonal Antibodies for the Treatment of Cancer

This example describes the use of mesothelin-specific human monoclonal antibodies for the treatment of cancers that exhibit overexpression of mesothelin (referred to herein as a "mesothelin-positive" cancer), including, but not limited to mesothelioma, prostate cancer, lung cancer, stomach cancer, squamous cell carcinoma, pancreatic cancer or ovarian cancer. Patients diagnosed with a mesothelin-positive cancer can be treated according to standard procedures in the art (see, for example, Hassan et al., *Proc. Am. Soc. Clin. Oncol.* 21:29a, 2002; Kreiman et al., *Proc. Am. Soc. Clint Oncol.* 21:22b, 2002).

In this example, patients diagnosed with a mesothelin-positive cancer are administered an immunoconjugate comprising a mesothelin-specific human monoclonal antibody linked to *Pseudomonas* exotoxin (PE). Preparation of PE immunoconjugates has been described (see, for example, U.S. Pat. No. 7,081,518 and U.S. Patent Application Publication No. 2005/0214304). In some patients, the immunoconjugate is administered by intravenous bolus injection every other day for a total of three to six doses. In other patients, the immunoconjugate is administered by continuous intravenous infusion over the course of ten days. The dose of immunoconjugate administered to a patient varies depending on the weight and gender of the patient, and mode and time course of administration. Following treatment, patients are evaluated for cancer progression (including tumor growth and metastasis) and other clinical signs of illness.

This disclosure provides fully human monoclonal antibodies specific for mesothelin. The disclosure further provides methods of treating or detecting cancers associated with expression of human mesothelin. It will be apparent that the precise details of the methods described may be varied or modified without departing from the spirit of the described disclosure. We claim all such modifications and variations that fall within the scope and spirit of the claims below.

The invention claimed is:

1. An isolated human monoclonal antibody that specifically binds human mesothelin with a binding affinity of about 20 nM or less, wherein:

(i) the light chain of the antibody comprises amino acids 27-32 of SEQ ID NO: 1, amino acids 50-52 of SEQ ID NO: 1 and amino acids 89-98 of SEQ ID NO: 1; and (ii) the heavy chain of the antibody comprises amino acids 26-35 of SEQ ID NO: 2, amino acids 53-59 of SEQ ID NO: 2 and amino acids 98-109 of SEQ ID NO: 2.

2. The isolated human monoclonal antibody of claim 1, wherein the light chain of the antibody comprises SEQ ID NO: 1, or the heavy chain of the antibody comprises SEQ ID NO: 2.

3. The isolated human monoclonal antibody of claim 1, wherein the light chain of the antibody comprises SEQ ID NO: 1, and the heavy chain of the antibody comprises SEQ ID NO: 2.

4. The isolated human monoclonal antibody of claim 1, wherein the antibody is a Fab fragment, a Fab' fragment, a $F(ab)'_2$ fragment, a single chain Fv protein ("scFv"), or a disulfide stabilized Fv protein ("dsFv").

5. The isolated human monoclonal antibody of claim 4, wherein the antibody is a Fab fragment.

6. The isolated human monoclonal antibody of claim 1, wherein the antibody is an IgG.

7. The isolated human monoclonal antibody of claim 1, wherein the antibody is labeled.

8. A composition comprising a therapeutically effective amount of the antibody of claim 1 in a pharmaceutically acceptable carrier.

9. An isolated immunoconjugate comprising the human monoclonal antibody of claim 1 and an effector molecule.

10. The isolated immunoconjugate of claim 9, wherein the effector molecule is a toxin or a detectable label.

11. A composition comprising a therapeutically effective amount of the isolated immunoconjugate of claim 9 in a pharmaceutically acceptable carrier.

12. A method of treating a subject with cancer, wherein the cancer is mesothelioma, prostate cancer, lung cancer, stomach cancer, squamous cell carcinoma, pancreatic cancer or ovarian cancer, comprising administering to the subject a therapeutically effective amount of the composition of claim 8, thereby treating the cancer in the subject.

13. A method of determining if a subject has cancer, wherein the cancer is mesothelioma, prostate cancer, lung cancer, stomach cancer, squamous cell carcinoma, pancreatic cancer or ovarian cancer, comprising:

contacting a sample from the subject with the isolated human monoclonal antibody of claim 1; and detecting binding of the antibody to the sample, wherein an increase in binding of the antibody to the sample as compared to binding of the antibody to a control sample identifies the subject as having cancer.

14. A method of confirming a diagnosis of cancer in a subject, wherein the cancer is mesothelioma, prostate cancer, lung cancer, stomach cancer, squamous cell carcinoma, pancreatic cancer or ovarian cancer, comprising:

contacting a sample from a subject diagnosed with cancer with the isolated human monoclonal antibody of claim 1; and detecting binding of the antibody to the sample, wherein an increase in binding of the antibody to the sample as compared to binding of the antibody to a control sample confirms the diagnosis of cancer in the subject.

15. The method of claim 13, wherein the isolated human monoclonal antibody is directly labeled.

16. The method of claim 13, further comprising:

contacting a second antibody that specifically binds the isolated human monoclonal antibody with the sample, and detecting the binding of the second antibody, wherein an increase in binding of the second antibody to the sample as compared to binding of the second antibody to a control sample detects cancer in the subject or confirms the diagnosis of cancer in the subject.

17. The method of claim 13, wherein the control sample is a sample from a subject without cancer.

18. The method of claim 13, wherein the sample is a blood, urine, biopsy, serum, sputum, plasma, cerebral spinal fluid sample.

19. An isolated nucleic acid molecule encoding the human monoclonal antibody of claim 1.

20. The isolated nucleic acid molecule of claim 19, wherein the nucleotide sequence encoding the light chain of the human monoclonal antibody comprises SEQ ID NO: 6, and the nucleotide sequence encoding the heavy chain of the human monoclonal antibody comprises SEQ ID NO: 7.

21. The isolated nucleic acid molecule of claim 19, operably linked to a promoter.

22. An expression vector comprising the isolated nucleic acid molecule of claim 19.

23. An isolated host cell transformed with the nucleic acid molecule of claim 19.

* * * * *

SEQUENCE LISTING

<160> NUMBER OF SEQ ID NOS: 8

<210> SEQ ID NO 1
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 1

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Gly Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 2
<211> LENGTH: 230
<212> TYPE: PRT
<213> ORGANISM: Artificial Sequence
<220> FEATURE:
<223> OTHER INFORMATION: Synthetic polypeptide

<400> SEQUENCE: 2

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80
```

-continued

```
Ser Leu Lys Leu Ser Ser Val Thr Ala Ala Asp Thr Ala Val Tyr Tyr
                85                  90                  95

Cys Ala Arg Glu Gly Lys Asn Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr Ser Gly Gln Ala Gly
225                 230


<210> SEQ ID NO 3
<211> LENGTH: 2187
<212> TYPE: DNA
<213> ORGANISM: Homo sapiens
<220> FEATURE:
<221> NAME/KEY: CDS
<222> LOCATION: (169)..(2037)

<400> SEQUENCE: 3

tgccaggctc tccaccccca cttcccaatt gaggaaaccg aggcagagga ggctcagcgc      60

cacgcactcc tctttctgcc tggccggcca ctcccgtctg ctgtgacgcg cggacagaga     120

gctaccggtg gacccacggt gcctccctcc ctgggatcta cacagacc atg gcc ttg      177
                                                     Met Ala Leu
                                                     1

cca acg gct cga ccc ctg ttg ggg tcc tgt ggg acc ccc gcc ctc ggc      225
Pro Thr Ala Arg Pro Leu Leu Gly Ser Cys Gly Thr Pro Ala Leu Gly
    5                   10                  15

agc ctc ctg ttc ctg ctc ttc agc ctc gga tgg gtg cag ccc tcg agg      273
Ser Leu Leu Phe Leu Leu Phe Ser Leu Gly Trp Val Gln Pro Ser Arg
20                  25                  30                  35

acc ctg gct gga gag aca ggg cag gag gct gcg ccc ctg gac gga gtc      321
Thr Leu Ala Gly Glu Thr Gly Gln Glu Ala Ala Pro Leu Asp Gly Val
                40                  45                  50

ctg gcc aac cca cct aac att tcc agc ctc tcc cct cgc caa ctc ctt      369
Leu Ala Asn Pro Pro Asn Ile Ser Ser Leu Ser Pro Arg Gln Leu Leu
            55                  60                  65

ggc ttc ccg tgt gcg gag gtg tcc ggc ctg agc acg gag cgt gtc cgg      417
Gly Phe Pro Cys Ala Glu Val Ser Gly Leu Ser Thr Glu Arg Val Arg
        70                  75                  80

gag ctg gct gtg gcc ttg gca cag aag aat gtc aag ctc tca aca gag      465
Glu Leu Ala Val Ala Leu Ala Gln Lys Asn Val Lys Leu Ser Thr Glu
    85                  90                  95

cag ctg cgc tgt ctg gct cac cgg ctc tct gag ccc ccc gag gac ctg      513
Gln Leu Arg Cys Leu Ala His Arg Leu Ser Glu Pro Pro Glu Asp Leu
100                 105                 110                 115

gac gcc ctc cca ttg gac ctg ctg cta ttc ctc aac cca gat gcg ttc      561
Asp Ala Leu Pro Leu Asp Leu Leu Leu Phe Leu Asn Pro Asp Ala Phe
                120                 125                 130
```

-continued

```
tcg ggg ccc cag gcc tgc acc cat ttc ttc tcc cgc atc acg aaa gcc      609
Ser Gly Pro Gln Ala Cys Thr His Phe Phe Ser Arg Ile Thr Lys Ala
            135                 140                 145

aat gtg gac ctg ctc ccg agg ggg gct ccc gag cga cag cgg ctg ctg      657
Asn Val Asp Leu Leu Pro Arg Gly Ala Pro Glu Arg Gln Arg Leu Leu
        150                 155                 160

cct gcg gct ctg gcc tgc tgg ggt gtg cgg ggg tct ctg ctg agc gag      705
Pro Ala Ala Leu Ala Cys Trp Gly Val Arg Gly Ser Leu Leu Ser Glu
    165                 170                 175

gct gat gtg cgg gct ctg gga ggc ctg gct tgc gac ctg cct ggg cgc      753
Ala Asp Val Arg Ala Leu Gly Gly Leu Ala Cys Asp Leu Pro Gly Arg
180                 185                 190                 195

ttt gtg gcc gag tcg gcc gaa gtg ctg cta ccc cgg ctg gtg agc tgc      801
Phe Val Ala Glu Ser Ala Glu Val Leu Leu Pro Arg Leu Val Ser Cys
                200                 205                 210

ccg gga ccc ctg gac cag gac cag cag gag gca gcc agg gcg gct ctg      849
Pro Gly Pro Leu Asp Gln Asp Gln Gln Glu Ala Ala Arg Ala Ala Leu
            215                 220                 225

cag ggc ggg gga ccc ccc tac ggc ccc ccg tcg aca tgg tct gtc tcc      897
Gln Gly Gly Gly Pro Pro Tyr Gly Pro Pro Ser Thr Trp Ser Val Ser
        230                 235                 240

acg atg gac gct ctg cgg ggc ctg ctg ccc gtg ctg ggc cag ccc atc      945
Thr Met Asp Ala Leu Arg Gly Leu Leu Pro Val Leu Gly Gln Pro Ile
    245                 250                 255

atc cgc agc atc ccg cag ggc atc gtg gcc gcg tgg cgg caa cgc tcc      993
Ile Arg Ser Ile Pro Gln Gly Ile Val Ala Ala Trp Arg Gln Arg Ser
260                 265                 270                 275

tct cgg gac cca tcc tgg cgg cag cct gaa cgg acc atc ctc cgg ccg     1041
Ser Arg Asp Pro Ser Trp Arg Gln Pro Glu Arg Thr Ile Leu Arg Pro
                280                 285                 290

cgg ttc cgg cgg gaa gtg gag aag aca gcc tgt cct tca ggc aag aag     1089
Arg Phe Arg Arg Glu Val Glu Lys Thr Ala Cys Pro Ser Gly Lys Lys
            295                 300                 305

gcc cgc gag ata gac gag agc ctc atc ttc tac aag aag tgg gag ctg     1137
Ala Arg Glu Ile Asp Glu Ser Leu Ile Phe Tyr Lys Lys Trp Glu Leu
        310                 315                 320

gaa gcc tgc gtg gat gcg gcc ctg ctg gcc acc cag atg gac cgc gtg     1185
Glu Ala Cys Val Asp Ala Ala Leu Leu Ala Thr Gln Met Asp Arg Val
    325                 330                 335

aac gcc atc ccc ttc acc tac gag cag ctg gac gtc cta aag cat aaa     1233
Asn Ala Ile Pro Phe Thr Tyr Glu Gln Leu Asp Val Leu Lys His Lys
340                 345                 350                 355

ctg gat gag ctc tac cca caa ggt tac ccc gag tct gtg atc cag cac     1281
Leu Asp Glu Leu Tyr Pro Gln Gly Tyr Pro Glu Ser Val Ile Gln His
                360                 365                 370

ctg ggc tac ctc ttc ctc aag atg agc cct gag gac att cgc aag tgg     1329
Leu Gly Tyr Leu Phe Leu Lys Met Ser Pro Glu Asp Ile Arg Lys Trp
            375                 380                 385

aat gtg acg tcc ctg gag acc ctg aag gct ttg ctt gaa gtc aac aaa     1377
Asn Val Thr Ser Leu Glu Thr Leu Lys Ala Leu Leu Glu Val Asn Lys
        390                 395                 400

ggg cac gaa atg agt cct cag gtg gcc acc ctg atc gac cgc ttt gtg     1425
Gly His Glu Met Ser Pro Gln Val Ala Thr Leu Ile Asp Arg Phe Val
    405                 410                 415

aag gga agg ggc cag cta gac aaa gac acc cta gac acc ctg acc gcc     1473
Lys Gly Arg Gly Gln Leu Asp Lys Asp Thr Leu Asp Thr Leu Thr Ala
420                 425                 430                 435

ttc tac cct ggg tac ctg tgc tcc ctc agc ccc gag gag ctg agc tcc     1521
Phe Tyr Pro Gly Tyr Leu Cys Ser Leu Ser Pro Glu Glu Leu Ser Ser
                440                 445                 450
```

-continued

```
gtg ccc ccc agc agc atc tgg gcg gtc agg ccc cag gac ctg gac acg      1569
Val Pro Pro Ser Ser Ile Trp Ala Val Arg Pro Gln Asp Leu Asp Thr
            455                 460                 465

tgt gac cca agg cag ctg gac gtc ctc tat ccc aag gcc cgc ctt gct      1617
Cys Asp Pro Arg Gln Leu Asp Val Leu Tyr Pro Lys Ala Arg Leu Ala
        470                 475                 480

ttc cag aac atg aac ggg tcc gaa tac ttc gtg aag atc cag tcc ttc      1665
Phe Gln Asn Met Asn Gly Ser Glu Tyr Phe Val Lys Ile Gln Ser Phe
    485                 490                 495

ctg ggt ggg gcc ccc acg gag gat ttg aag gcg ctt agt cag cag aat      1713
Leu Gly Gly Ala Pro Thr Glu Asp Leu Lys Ala Leu Ser Gln Gln Asn
500                 505                 510                 515

gtg agc atg gac ttg gcc acg ttc atg aag ctg cgg acg gat gcg gtg      1761
Val Ser Met Asp Leu Ala Thr Phe Met Lys Leu Arg Thr Asp Ala Val
                520                 525                 530

ctg ccg ttg act gtg gct gag gtg cag aaa ctt ctg gga ccc cac gtg      1809
Leu Pro Leu Thr Val Ala Glu Val Gln Lys Leu Leu Gly Pro His Val
            535                 540                 545

gag ggc ctg aag gcg gag gag cgg cac cgc ccg gtg cgg gac tgg atc      1857
Glu Gly Leu Lys Ala Glu Glu Arg His Arg Pro Val Arg Asp Trp Ile
        550                 555                 560

cta cgg cag cgg cag gac gac ctg gac acg ctg ggg ctg ggg cta cag      1905
Leu Arg Gln Arg Gln Asp Asp Leu Asp Thr Leu Gly Leu Gly Leu Gln
    565                 570                 575

ggc ggc atc ccc aac ggc tac ctg gtc cta gac ctc agc gtg caa gag      1953
Gly Gly Ile Pro Asn Gly Tyr Leu Val Leu Asp Leu Ser Val Gln Glu
580                 585                 590                 595

gcc ctc tcg ggg acg ccc tgc ctc cta gga cct gga cct gtt ctc acc      2001
Ala Leu Ser Gly Thr Pro Cys Leu Leu Gly Pro Gly Pro Val Leu Thr
                600                 605                 610

gtc ctg gca ctg ctc cta gcc tcc acc ctg gcc tga gggccccact           2047
Val Leu Ala Leu Leu Leu Ala Ser Thr Leu Ala
            615                 620

cccttgctgg ccccagccct gctggggatc cccgcctggc caggagcagg cacgggtggt   2107

ccctgttcca ccccaagaga actcgcgctc agtaaacggg aacatgcccc ctgcaaaaaa   2167

aaaaaaaaaa aaaaaaaaaa                                                2187


<210> SEQ ID NO 4
<211> LENGTH: 622
<212> TYPE: PRT
<213> ORGANISM: Homo sapiens

<400> SEQUENCE: 4

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110
```

-continued

```
Glu Asp Leu Asp Ala Leu Pro Leu Asp Leu Leu Leu Phe Leu Asn Pro
        115                 120                 125

Asp Ala Phe Ser Gly Pro Gln Ala Cys Thr His Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540
```

```
Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Val Gln Glu Ala Leu Ser Gly Thr Pro Cys Leu Leu Gly Pro Gly Pro
        595                 600                 605

Val Leu Thr Val Leu Ala Leu Leu Leu Ala Ser Thr Leu Ala
    610                 615                 620


<210> SEQ ID NO 5
<211> LENGTH: 4
<212> TYPE: PRT
<213> ORGANISM: Artificial
<220> FEATURE:
<223> OTHER INFORMATION: Synthetic polypeptide

<400> SEQUENCE: 5

Ala Asp Pro Gly
1


<210> SEQ ID NO 6
<211> LENGTH: 642
<212> TYPE: DNA
<213> ORGANISM: Artificial Sequence
<220> FEATURE:
<223> OTHER INFORMATION: Synthetic polynucleotide

<400> SEQUENCE: 6

gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

gggttcagtg gcagtggatc tgggacagat ttcactctca ccatcagcag tctgcaacct    240

gaagattttg caacttacta ctgtcaacag agttacagta ccccgctcac tttcggcgga    300

gggaccaagg tggagatcaa acgaactgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctact gcctcagcag caccctgacg    540

ctgagcaaag cagactacga gaaacacaaa ctctacgcct gcgaagtcac ccatcagggc    600

ctgagctcgc ccgtcacaaa gagcttcaac aggggagagt gt                       642


<210> SEQ ID NO 7
<211> LENGTH: 693
<212> TYPE: DNA
<213> ORGANISM: Artificial Sequence
<220> FEATURE:
<223> OTHER INFORMATION: Synthetic polynucleotide

<400> SEQUENCE: 7

caggtgcagc tgcaggagtc cggcccagga ctggtgaagc cttcggagac cctgtccctc     60

acctgcactg tctctggtgg ctccgtcagc agtggtagtt actactggag ctggatccgg    120

cagcccccag ggaagggact ggagtggatt gggtatatct attacagtgg gagcaccaac    180

tacaacccct ccctcaagag tcgagtcacc atatcagtag acacgtccaa gaaccagttc    240

tccctgaagc tgagctctgt gaccgctgcg gacacggccg tgtattactg tgcgagagag    300
```

-continued

```
gggaagaatg gggcttttga tatctggggc caagggacaa tggtcaccgt ctcttcagcc    360

tccaccaagg gcccatcggt cttcccctg gcaccctcct ccaagagcac ctctgggggc    420

acagcggccc tgggctgcct ggtcaaggac tacttccccg aaccggtgac ggtgtcgtgg    480

aactcaggcg ccctgaccag cggcgtgcac accttcccgg ctgtcctaca gtcctcagga    540

ctctactccc tcagcagcgt ggtgaccgtg ccctccagca gcttgggcac ccagacctac    600

atctgcaacg tgaatcacaa gcccagcaac accaaggtgg acaagaaagt tgagcccaaa    660

tcttgtgaca aaactagtgg ccaggccggc cac                                  693


<210> SEQ ID NO 8
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 8

Gly Gly Gly Gly Ser
1               5
```